United States Patent
Shen et al.

(10) Patent No.: US 7,790,161 B2
(45) Date of Patent: Sep. 7, 2010

(54) GDF-9/BMP-15 MODULATORS FOR THE TREATMENT OF BONE DISORDERS

(75) Inventors: Emily Sheng-Ming Shen, West Chester, PA (US); Frederick J. Bex, Newtown Square, PA (US); Yogendra P. Kharode, Media, PA (US); Vargheese M. Chennathukuzhi, Collegeville, PA (US); Murty V. Chengalvala, Audubon, PA (US); Ashok Bapat, Blue Bell, PA (US); Panayiotis E. Stevis, Glenmoore, PA (US); Gregory S. Kopf, Villanova, PA (US)

(73) Assignee: Wyeth LLC, Madison, NJ (US)

( * ) Notice: Subject to any disclaimer, the term of this patent is extended or adjusted under 35 U.S.C. 154(b) by 65 days.

(21) Appl. No.: 11/691,824

(22) Filed: Mar. 27, 2007

(65) Prior Publication Data

US 2007/0237778 A1 Oct. 11, 2007

Related U.S. Application Data

(60) Provisional application No. 60/787,246, filed on Mar. 28, 2006.

(51) Int. Cl.
*A61K 39/00* (2006.01)
*A61K 39/395* (2006.01)
*A61K 38/18* (2006.01)
*A61K 38/19* (2006.01)
*A61K 38/22* (2006.01)
*A61K 38/29* (2006.01)

(52) U.S. Cl. .............. 424/130.1; 424/133.1; 424/135.1; 424/139.1; 424/141.1; 424/142.1; 424/143.1; 424/145.1; 424/158.1; 514/2; 514/7; 514/8; 514/44

(58) Field of Classification Search .................. None
See application file for complete search history.

(56) References Cited

U.S. PATENT DOCUMENTS

| 4,970,237 A * | 11/1990 | Jensen et al. ............. 514/651 |
| 5,635,372 A | 6/1997 | Celeste et al. |
| 5,728,679 A | 3/1998 | Celeste et al. |
| 6,030,617 A * | 2/2000 | Lee ...................... 424/158.1 |
| 2003/0162714 A1 | 8/2003 | Hill et al. |
| 2003/0180306 A1 | 9/2003 | Hill et al. |

FOREIGN PATENT DOCUMENTS

| WO | WO 94/15966 | 7/1994 |
| WO | WO 99/17797 | 4/1999 |
| WO | WO 99/50672 | 10/1999 |
| WO | WO 02/100426 | 12/2002 |
| WO | WO 2004/111036 | 12/2004 |

OTHER PUBLICATIONS

Toda et al., 2002, Eur. J. Biochem. 269:22214-2222.*
Riggs et al. (1986, J. Clin. Invest. 77:1487-1491).*
Gilchrist et al., Biol. Reprod. 71:732-739 (2004).
International Search Report for PCT/US2007/065012, dated Mar. 7, 2008.
Written Opinon of Int'l Searching Authority in PCT/US2007/065012, dated Mar. 7, 2008.
Bogdanovich et al. (2002) "Functional improvement of dystrophic muscle by myostatin blockade," *Nature* 420:418-421.
Dong et al. (1996) "Growth differentiation favtor-9 is required during early ovarian folliculogenesis," *Nature* 383:531-535.
McPherron et al. (1997) "Regulation of skeletal muscle mass in mice by a new TGF-β superfamily member," *Nature* 387:83-90.
Morrison et al. (2009) "A soluble activin type IIB receptor improves function in a mouse model of amyotrophic lateral sclerosis," *Exp. Neurol.* 217:258-268.

* cited by examiner

*Primary Examiner*—Elizabeth C. Kemmerer

(57) ABSTRACT

The invention provides methods for treating or preventing bone degenerative disorders. The disorders treated or prevented include, for example, osteopenia, osteomalacia, osteoporosis, osteomyeloma, osteodystrophy, Paget's disease, osteogenesis imperfecta, and bone degenerative disorders associated with chronic renal disease, hyperparathyroidism, and long-term use of corticosteroids. The disclosed therapeutic methods include administering to a mammal an inhibitor of GDF-9 or BMP-15 in an amount effective to: (1) treat or prevent a bone degenerative disorder; (2) slow bone deterioration; (3) restore lost bone; (4) stimulate new bone formation; and/or (5) maintain bone mass and/or bone quality. The invention also provides methods for administering a GDF-9 agonist or a BMP-15 agonist to treat a bone disorder characterized by increased bone density or mass.

38 Claims, No Drawings

GDF-9/BMP-15 MODULATORS FOR THE TREATMENT OF BONE DISORDERS

PRIOR APPLICATIONS

This application claims priority to U.S. Provisional Application No. 60/787,246, filed Mar. 28, 2006, the disclosure of which is hereby incorporated by reference.

TECHNICAL FIELD

The technical field of the invention relates to the therapeutic uses of GDF-9 and BMP-15 modulators in the treatment of bone disorders such as osteoporosis, osteopenia, osteomalacia, osteodystrophy, and bone fracture.

BACKGROUND OF THE INVENTION

Members of the transforming growth factor-beta (TGF-β) superfamily possess physiologically important growth-regulatory and morphogenetic properties (Kingsley et al., *Genes Dev.* 8:133-146 (1994); Hoodless et al., *Curr. Topics Microbiol. Immunol.* 228:235-272 (1998)). Considerable attention has focused in recent years on the role of two TGF-β superfamily members in ovarian function and fertility: growth and differentiation factor-9 (GDF-9) and bone morphogenetic protein-15 (BMP-15, also known as GDF-9b; McNatty et al., *Reprod.* 128:379-386 (2004); Juengel et al., *Hum Reprod. Upd.* 11:144-161 (2005)).

GDF-9 was first described in 1993 as a novel member of the TGF-β superfamily which is specifically expressed in the ovary (McPherron et al., *J. Biol. Chem.* 268:3444-3449 (1993)). Like other members of the TGF-β family, GDF-9 is encoded as a prepropeptide consisting of a signal peptide, a proregion, and a C-terminal mature region which is cleaved from the precursor peptide by an intracellular protease belonging to a group of furin-like proteases. GDF-9 mRNA is present in oocytes at all stages of folliclular development, and is expressed from the primary follicle stage until after ovulation (McPherron and Lee, *J. Biol. Chem.* 268: 3444-3449 (1993); McGrath et al., *Mol. Endocrinol.* 9:131-136 (1995); Elvin et al., *Mol. Endocrinol.* 13:1035-1048 (1999)). Female mice lacking GDF-9 are infertile due to the arrest of developing oocytes at the primary follicle stage (Dong et al., *Nature* 383:531-535 (1996); Carabatsos et al., *Dev. Biol.* 204: 373-384 (1998)).

BMP-15, also known as GDF-9b, was discovered as an X-linked gene that encodes a homologue of GDF-9, sharing 52% amino acid identity to GDF-9 in the mature regions (Dube et al., *Mol. Endocrinol.* 12:1809-1817 (1998); Laitinen et al., *Mech. Dev.* 78:135-140 (1998)). Although BMP-15 expression is identical to that of GDF-9, it cannot compensate for absence of GDF-9 in a GDF-9 knockout mouse. Female mice lacking BMP-15 are subfertile, demonstrating reduced lifter sizes and litters per month (Yan et al., *Mol. Endocrinol.* 15: 854-866 (2001)). In sheep, both GDF-9 and BMP-15 are essential for fertility (Juengel et al., *Bio. Reprod.* 67: 1777-1789 (2002)). Naturally occurring BMP-15 mutations in sheep cause infertility in homozygous females. BMP-15 also plays a critical role in human female fertility, as a BMP-15 mutation has been associated with ovarian dysgenesis in women (Di Pasquale et al., *Am. J. Hum. Genet.* 75:106-111 (2004)).

GDF-9 and BMP-15 are unique among members of the TGF-β family described to date in that they lack the fourth of seven characteristic conserved cysteine residues in the mature region (Dube et al., *Mol. Endocrinol.* 12:1809-1817 (1998); Laitinen et al., *Mech. Dev.* 78:135-140 (1998)). The fourth cysteine is of particular importance because it is responsible for forming the disulfide bond between the subunits of the mature dimer of most TGF-β family members. Although GDF-9 and BMP-15 lack this cysteine and do not form covalently linked dimers, studies have found that both GDF-9 and BMP-15 can form homodimers as well as heterodimers in vitro (Liao et al., *J. Biol. Chem.* 278:3713-3719 (2003); Liao et al., *J. Biol. Chem.* 279:17391-17396 (2004)).

Expression of both GDF-9 and BMP-15 is primarily restricted to the oocytes of growing follicles in mammals. Consistent with this expression pattern, no effects outside the ovary have been seen in animals carrying mutations in these genes, including sheep and mice, nor in sheep immunized with GDF-9 or BMP-15 peptides (Galloway et al., *Nat. Genet* 25:279-283 (2000); Hanrahan et al., *Biol. Reprod.* 121:843-852 (2004); Dong et al., *Nature* 383:531-535 (1996); Yan et al., *Mol. Enocrinol.* 15:854-866 (2001); Juengel et al., *Biol. Reprod.* 70:557-561 (2004); and Elvin et al., *Mol. Endocrinol.* 13:1018-1034 (1999)). Thus, these factors have been considered attractive targets for manipulating fertility with a low risk of non-ovarian side effects, including for the purpose of developing new clinical treatments for female infertility, for developing new non-steroidal contraceptives for women, and for modulating fertility in agricultural settings (see, e.g., U.S. Pat. No. 6,030,617).

Although primarily localized to the ovary, GDF-9 and BMP-15 expression have been observed in non-ovarian tissues, including the pituitary and testis (Fitzpatrick et al., *Endocrinol.* 139:2571-2578 (1998); Aaltonen et al., *J. Clin. Endocrinol. Metab.* 84:2744-2750 (1999); Eckery et al., *Mol. Cell. Endocrinol.* 192:115-126 (2002); Otsuka and Shimasaki, *Endocrinol.* 143:4938-4941 (2002)). However, because expression of these proteins is largely limited to the ovary, non-reproductive functions and uses for GDF-9 and BMP-15 have not received much attention.

A number of conditions are associated with a loss of bone, particularly in the elderly and/or postmenopausal women. For example, osteoporosis is a debilitating disease characterized by a decrease in skeletal bone mass and mineral density, structural deterioration of the bone, and corresponding increases in bone fragility and susceptibility to fracture. Osteoporosis in humans is preceded by clinical osteopenia, a condition found in approximately 25 million people in the United States.

Throughout adult life, bone continually undergoes a turnover through the coupled processes of bone formation and resorption. Bone resorption is mediated by bone resorbing cells, osteoclasts, which are formed by mononuclear phagocytic cells. New bone replacing the lost bone is deposited by bone-forming cells, osteoblasts, which are formed by mesenchymal stromal cells. Various other cell types that participate in the remodeling process are tightly controlled by systemic factors (e.g., hormones, lymphokines, growth factors, and vitamins) and local factors (e.g., cytokines, adhesion molecules, lymphokines, and growth factors). The proper spatiotemporal coordination of the bone remodeling process is essential to the maintenance of bone mass and integrity. A number of bone degenerative disorders are linked to an imbalance in the bone remodeling cycle which results in abnormal loss of bone mass (osteopenia) including metabolic bone diseases, such as osteoporosis, osteoplasia (osteomalacia), osteodystrophy, and Paget's disease.

There are currently two main types of pharmaceutical therapy available for the treatment of osteoporosis. The first, and most common, approach is the use of hormone therapy to reduce the resorption of bone tissue. Estrogen replacement therapy ("ERT") is known to prevent further deterioration and thus reduce the likelihood of fractures. However, the use of estrogen as a treatment is limited, as it is believed that long-term estrogen therapy may be associated with risk of uterine cancer, endometrial cancer, breast cancer, frequent vaginal bleeding, and thrombosis. Because of these serious side effects, many women choose to avoid this treatment. Further, few men agree to this type of therapy. The second major therapeutic approach to osteoporosis is the use of bisphosphonates, particularly alendronate, risedronate, and ibandronate. Although tests have shown that these compounds consistently increase the bone mineral density in osteoporosis patients, there are also significant problems with the treatment of osteoporosis by bisphosphonates, including irritation of the esophagus and upper gastrointestinal tract.

Therefore, there exists a need to develop new therapeutic methods for treating and preventing bone disorders.

SUMMARY OF THE INVENTION

GDF-9 affects bone density, including both cortical and trabecular bone mineral density. Accordingly, the invention provides methods for modulating GDF-9 to treat or prevent bone disorders by administering a modulator of GDF-9. The invention also provides methods for treating or preventing bone disorders by administering a modulator of BMP-15.

In one embodiment, an inhibitor of GDF-9 is administered to treat or prevent bone degenerative disorders. In an alternate embodiment, an inhibitor of BMP-15 is administered to treat or prevent bone degenerative disorders. The disorders treated or prevented may include, for example, osteopenia, osteomalacia, osteoporosis, osteomyeloma, osteodystrophy, Paget's disease, osteogenesis imperfecta, bone sclerosis, aplastic bone disorder, humoral hypercalcemic myeloma, multiple myeloma and bone thinning following metastasis. The disorders treated or prevented may further include bone degenerative disorders associated with hypercalcemia, chronic renal disease (including end-stage renal disease), kidney dialysis, primary or secondary hyperparathyroidism, inflammatory bowel disease, Krohn's disease, and long-term use of corticosteroids or GnRH agonists or antagonists.

The methods of the invention include administering to a mammal a GDF-9 or BMP-15 inhibitor in an amount effective to:

(1) treat or prevent a bone degenerative disorder;
(2) slow bone deterioration;
(3) restore lost bone;
(4) stimulate new bone formation; and/or
(5) maintain bone (bone mass and/or bone quality).

In some embodiments, the modulator is an inhibitor of GDF-9 or BMP-15, including, for example, an anti-GDF-9 antibody, an anti-BMP-15 antibody, an anti-GDF-9 receptor antibody, an anti-BMP-15 receptor antibody, a soluble GDF-9 receptor, a soluble BMP-15 receptor, a dominant negative GDF-9 peptide, or a dominant negative BMP-15 peptide. In certain embodiments, the inhibitor decreases expression of GDF-9 or BMP-15, including, for example, an siRNA.

The invention further provides assays for evaluating efficacy of a inhibitor of GDF-9 or BMP-15 for treatment of a bone degenerative disorder. Methods of administration, compositions, and devices used in the methods of the inventions are also provided.

The invention also provides methods for decreasing bone density by administering an agonist of GDF-9 or BMP-15. Disorders that may be treated include, for example, sclerosing bone dysplasias, skeletal bone dysplasias, such as osteopetrosis or osteosclerosis and endosteal hyperostosis; Camurati-Engelmann disease (associated with increased TGF-β signaling); Van Buchen disease and sclerosteosis (resulting in increased BMP signaling); autosonal dominant osteoscleorosis; autosonal dominant osteopetrosis type I; and Worth disease. Accordingly, the methods of the invention include administering to a mammal a GDF-9 or BMP-15 agonist in an amount effective to treat or prevent a bone dysplasia disorder.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEQUENCES

SEQ ID NO:1 is a nucleotide sequence of the human GDF-9 gene (see also Genbank Accession No. NM_005260).

SEQ ID NO:2 is an amino acid sequence of human GDF-9 (see also Genbank Accession No. NP_005251.1).

SEQ ID NO:3 is a nucleotide sequence of the human BMP-15 gene (see also Genbank Accession No. NM_005448).

SEQ ID NO:4 is an amino acid sequence of human BMP-15 (see also Genbank Accession No. NP_005439).

SEQ ID NO:5 is an amino acid sequence of a GDF-9 peptide.

DETAILED DESCRIPTION

The present invention provides methods of administering a modulator of GDF-9 or BMP-15 to mammals to treat or prevent bone disorders.

The methods of the invention can be used to treat or prevent a bone disorder in any mammals in need of such treatment, including specifically humans, primates, monkeys, rodents, sheep, rabbits, dogs, guinea pigs, horses, cows, and cats.

In certain embodiments, a GDF-9 inhibitor or BMP-15 inhibitor is administered to treat or prevent a bone degenerative disorder. The disorders treated or prevented by administration of a GDF-9 inhibitor or a BMP-15 inhibitor include, for example, osteopenia, osteomalacia, osteoporosis (e.g., post-menopausal, steroid-induced, senile, or thyroxin-use induced), osteomyeloma, osteodystrophy, Paget's disease, osteogenesis imperfecta, humoral hypercalcemic myeloma, multiple myeloma and bone thinning following metastatis. The disorders treated or prevented further include bone degenerative disorders associated with hypercalcemia, chronic renal disease, primary or secondary hyperparathyroidism, inflammatory bowel disease, Krohn's disease, long-term use of corticosteroids or GnRH agonists or antagonists, and nutritional deficiencies.

In other embodiments, a GDF-9 agonist or BMP-15 agonist is administered to treat or prevent a bone disorder including, for example, a disorder characterized by excessive bone growth or skeletal overgrowth, such as sclerosing bone dysplasias. This disorder, termed "sclerosteosis" is a progressive disorder characterized by general skeletal overgrowth, gigantism, entrapment of cranial nerves, increased intracranial pressure due to widening of the calvarium of the skull, and increased thickness and density of both trabecular and cortical bone. Disorders characterized by excessive bone growth or skeletal overgrowth include, but are not limited to, sclerosing bone dysplasias, skeletal bone depplasias, such as osteosclerosis, osteopetrosis, and endosteal hyperostosis; Camurati-Engelmann disease; Van Buchen disease and sclerosteosis; autosonal dominant osteosclerosis; autosonal dominant osteopetrosis type I; and Worth disease. See Wesenbeck et al., Am. J. Human Genet. 72: 763-771 (2003), and references cited therein.

In one embodiment, the invention provides methods to treat or prevent a bone degenerative disorder in a post-menopausal woman. One embodiment of the invention provides methods to treat or prevent a bone degenerative disorder in an individual with steroid-induced osteoporosis. The invention also provides methods to treat or prevent senile osteoporosis in an individual. Another embodiment of the invention provides methods to treat or prevent thyroxin-use or glucocorticoid-use induced osteoporosis in an individual.

The present invention provides methods to decrease fertility and simultaneously slow bone deterioration, maintain bone, restore lost bone, or stimulate new bone formation in a mammal. In another embodiment, the invention provides methods to decrease fertility and to simultaneously treat or prevent a bone degenerative disorder in a woman.

The invention also provides methods to treat or prevent a bone degenerative disorder in a man.

The disclosed methods include administering to a mammal an inhibitor of GDF-9 or an inhibitor of BMP-15 in an amount effective to:

(1) treat or prevent a bone degenerative disorder;
(2) slow bone deterioration;
(3) restore lost bone;
(4) stimulate new bone formation; and/or
(5) maintain bone (bone mass and/or bone quality).

The methods of the invention can be used to treat microdefects in trabecular and cortical bone. The bone quality can be determined, for example, by assessing microstructural integrity of the bone.

Generally, a modulator of GDF-9 or BMP-15 is administered repeatedly for a period of at least 2, 4, 6, 8, 10, 12, 20, or 40 weeks or for at least 1, 1.5, or 2 years or up to the life-time of the subject. In certain embodiments, a single bolus dose can be administered, for example by administration of an injectable or implantable composition, as described in detail below.

Generally, modulators of GDF-9 and BMP-15 useful in the methods of the invention, including inhibitors of GDF-9 or inhibitors of BMP-15, may be administered at a dose between 10-8 and 10-7; 10-7 and 10-6; 10-6 and 10-5; or 10-5 and 10-4 g/kg. Therapeutically effective dosages achieved in one animal model can be converted for use in another animal, including humans, using conversion factors known in the art (see, e.g., Freireich et al. (1966) Cancer Chemother. Reports, 50(4):219-244).

The exact dosage of a modulator used in a method of the invention is determined empirically based on the desired outcome(s). Exemplary outcomes include: (a) bone degenerative disorder is treated or prevented, (b) bone deterioration is slowed; (c) lost bone is restored; (d) new bone growth is formed; and/or (e) bone mass and/or bone quality is maintained. For example, a modulator is administered in an amount effective to slow bone deterioration (e.g., loss of bone mass and/or bone mineral density) by at least 10, 20, 30, 40, 50, 100, 200, 300, 400, or 500%.

In one embodiment of the invention, the modulator is able to exert the desired therapeutic effect on bone density without crossing the ovarian blood follicle barrier, which is both charge- and size-selective (Hess et al., Biol. Reprod. 58:705-711 (1998)). Such a differential effect for a modulator can be a function of its size, its charge, and/or its relative effective concentration in different tissues, for example following systemic administration.

The outcome(s) related to bone deterioration may also be evaluated by a specific effect of the modulators of GDF-9 and BMP-15 with respect to loss of trabecular bone (trabecular plate perforation); loss of (metaphyseal) cortical bone; loss of cancellous bone; decrease in bone mineral density, reduced bone mineral quality, reduced bone remodeling; increased level of serum alkaline phosphatase and acid phosphatase; bone fragility (increased rate of fractures), decreased fracture healing. Methods for evaluating bone mass and quality are known in the art and include, but are not limited to X-ray diffraction; DXA; DEQCT; PQCT, chemical analysis, density fractionation, histophotometry, histomorphometry, and histochemical analysis as described, for example, in Lane et al., J. Bone Min. Res. 18:2105-2115 (2003). One assay for determining cortical bone density is the MicroCT assay. Following pQCT measurement, the microCT evaluation can be performed, for example, using a Scanco mCT40 (Scanco Medical AG) on a femur.

The invention also provides methods for the measurement of bone formation by calcein labeling. For example, mice can be injected with calcein (e.g. 15 mg/kg, 0.1 ml/mouse, s.c.) on 9 and 2 days prior to tissue collection. Bone tissues can be collected from both femurs and tibia, as well as spine. Histological characterization of bone samples to measure the distance between calcein-labeled mineralized bone layers is used to evaluate bone formation.

Additional applications of the present invention include use of GDF-9 and/or BMP-15 modulators for coating, or incorporating into, osteoimplants, matrices, and depot systems so as to promote osteointegration. Examples of such implants include dental implants and joint replacements implants.

The invention further comprises assays for evaluating efficacy of a GDF-9 modulator or BMP-15 modulator for treatment of a bone degenerative disorder.

Such an assay comprises:

(1) administering the modulator repeatedly to a mammal (e.g., an OVX rat) for a period of at least 2, 4, 6, or 8 weeks; and
(2) determining the effect of the modulator on bone, wherein a slowing of bone deterioration (e.g., bone mass and/or bone quality) attributable to the modulator indicates that the modulator is effective for treatment of a bone degenerative disorder; and decreased bone density attributable to the modulator indicates that the modulator is effective for treatment of a sclerosing bone dysplasia or disorders of inappropriately elevated bone mass.

It will be understood that a modulator of GDF-9 or BMP-15 may be evaluated in one or more animal models of bone disorders, including bone degenerative disorders, and/or in humans. Osteopenia may be induced, for example, by immobilization, low calcium diet, high phosphorus diet, long term use of corticosteroid, or GnRH agonist or antagonist, cessation of ovary function, or aging. For example, ovariectomy (OVX)-induced osteopenia is a well established animal model of human post-menopausal osteoporosis. Another well validated model involves administration of corticosteroids. Such models include: cynomolgus monkeys, dogs, mice, rabbits, ferrets, guinea pigs, minipigs, and sheep. For a review of various animal models of osteoporosis, see, e.g., Turner, Eur. Cells and Materials 1:66-81 (2001).

Additional in vitro tests may include evaluation of the effect on osteoblasts in culture such as the effect on collagen and osteocalcin synthesis or the effect on the level of alkaline phosphatase and cAMP induction. Appropriate in vivo and in vitro tests are described in, for example, U.S. Pat. No. 6,333,312.

I. GDF-9 and BMP-15 Modulators

GDF-9 is synthesized as a prepropolypeptide of about 454 amino acids (aa) (SEQ ID No: 2), including a 27 amino acid signal sequence and a 292 amino acid propeptide. The mature C-terminal fragment of GDF-9 is predicted to be 135 amino acids in length and to have an unglycosylated molecular weight of about 15.6 kD, as determined by nucleotide sequence analysis. GDF-9 signaling is mediated through the type I receptor ALK5 (Mazerbourg et al., *Mol. Endocrinol.* 18:653-665 (2004)) and the type II receptor BMPRII (Vitt et al., *Biol. Reprod.* 67:473-480 (2002)). The amino acid sequence of mature human GDF-9 is contained within SEQ ID NO:2 (GenBank Accession No. NP_005251.1). The sequence of the human GDF-9 wild type gene is disclosed, for example, in GenBank Accession No. NM_005260, U.S. Pat. Nos. 5,821,056; 6,191,261; and 6,365,402, as well as in U.S. Patent Pub. Nos. 2002/0127612 and 2004/0152143. The nucleotide sequence of the mouse GDF-9 gene is found in GenBank Accession No. NM_008110; nucleotides 29-1354 encode the mouse GDF-9 protein (GenBank Accession No. NP_032136.1). The nucleotide sequence of the rat GDF-9 gene is found in GenBank Accession No. NM_021672; nucleotides 1-1323 encode the rat GDF-9 protein (GenBank Accession No. NP_067704.1).

BMP-15 is synthesized as a prepropolypeptide of about 392 amino acids (SEQ ID No: 4; GenBank Accession No. NP_005439.1), including an 18 amino acid signal sequence and a 249 amino acid propeptide; nucleotide residues 1 to 1179 encode SEQ ID NO:4. The mature C-terminal fragment of BMP-15 is predicted to be 125 amino acids in length, and consists of amino acid residues 268-392 of the prepropolypeptide. BMP-15 signaling is mediated through the type I receptor ALK6 and the type II receptor BMPRII (Moore et al., *J. Biol. Chem.* 278:304-310 (2003)). The amino acid sequence of mature human BMP-15 is contained within SEQ ID NO:4. The sequence of the human BMP-15 (GDF-9b) wild type gene is disclosed, for example, in GenBank Accession No. NM_005448, U.S. Pat. Nos. 5,728,679 and 5,635,372, and U.S. Patent Pub. No. 2004/0092007. The nucleotide sequence of the mouse BMP-15 gene is found in GenBank Accession No. NM_009757; nucleotides 358-1536 encode the mouse BMP-15 protein (GenBank Accession No. NP_033887). The nucleotide sequence of the rat BMP-15 gene is found in GenBank Accession No. NM_021670; nucleotides 247-1422 encode the rat BMP-15 protein (GenBank Accession No. NP_067702.1).

The terms "GDF-9" and "BMP-15," as used herein, refer to any one or more isoforms of GDF-9 or BMP-15, respectively. The terms refer to the full length unprocessed precursor form of GDF-9 or BMP-15, as well as the mature and propeptide forms resulting from post-translational cleavage. The term "propeptide" refers to the polypeptide that is cleaved from the amino-terminal domain of the GDF-9 or BMP-15 precursor protein. The term "mature protein" refers to the protein that is cleaved from the carboxy-terminal domain of the GDF-9 or BMP-15 precursor protein. Mature GDF-9 may be present as a monomer, homodimer, or in a heterodimer, for example with BMP-15. Mature BMP-15 may be present as a monomer, homodimer, or in a heterodimer. Depending on conditions, the mature protein may establish equilibrium between any or all of these different forms. In its biologically active form, mature GDF-9 is also referred to as "active GDF-9;" mature BMP-15 is also referred to as "active BMP-15." The terms also refer to any fragments and variants of GDF-9 or BMP-15 that maintain at least some biological activities associated with mature GDF-9 or BMP-15, as discussed herein, including sequences that have been modified. The present invention may employ modulators of GDF-9 and BMP-15 from all vertebrate species, including but not limited to human, bovine, chicken, mouse, rat, porcine, ovine, turkey, baboon, and fish.

The terms "GDF-9 receptor" and "BMP-15 receptor," unless otherwise indicated, refer to any receptor that binds at least one GDF-9 or BMP-15 isoform, respectively. The structural and functional aspects of GDF-9 and BMP-15, as well as their receptors, are well known in the art (see, for example, Chang et al., Endocrine *Rev.* 23:787-823 (2002); Moore et al., *Molec. Cell. Endocrinol.* 234:67-73 (2005); Juengel et al., *Hum. Reprod. Update* 11:144-161 (2004)).

A. GDF-9 and BMP-15 Inhibitors

The term "GDF-9 inhibitor" and its cognates such as "antagonist," "neutralizing," and "downregulating" refer to a compound (or its property as appropriate), which acts as an inhibitor of biological activity of GDF-9. A GDF-9 inhibitor may, for example, bind to and neutralize the activity of GDF-9; decrease GDF-9 expression levels; affect stability or conversion of the precursor molecule to the active, mature form; interfere with the binding of GDF-9 to one or more receptors; or it may interfere with intracellular signaling of a GDF-9 receptor. The term "direct GDF-9 inhibitor" generally refers to any compound that directly downregulates the biological activity of GDF-9. A molecule "directly downregulates" the biological activity of GDF-9 if it downregulates the activity by interacting with a GDF-9 gene, a GDF-9 transcript, a GDF-9 ligand, or a GDF-9 receptor. The terms "neutralize," "neutralizing," "inhibitory," and their cognates refer to a reduction in the activity of GDF-9 by a GDF-9 inhibitor, relative to the activity of GDF-9 in the absence of the same inhibitor. The reduction in activity is preferably at least about 10%, 20%, 30%, 40%, 50%, 60%, 70%, 80%, 90%, or higher. Methods to identify agents which alter the activity of GDF-9 are described in U.S. Pat. No. 6,680,174, for example to alter female fertility.

GDF-9 inhibitors that can block the activity of GDF-9 are useful in the methods of the invention. Such inhibitors may interact with GDF-9 itself. Alternatively, inhibitors may interact with a GDF-9 receptor (such as ALK5 or BMPRII) or other binding partner, for example. Inhibitors may reduce or and may be effective in the invention if they block the binding of GDF-9 to its receptor and/or if they block the activity of the receptor after binding of GDF-9. Inhibitors, of course, may interact with both GDF-9 and a second factor, such as its receptor. In this regard, GDF-9 inhibitors include antibodies (against GDF-9 and/or a GDF-9 receptor), modified soluble receptors, other proteins (including those that bind to GDF-9 and/or a GDF-9 receptor), modified forms of GDF-9 or fragments thereof, propeptides, peptides, and mimetics of all of these inhibitors. Nonproteinaceous inhibitors include, for example, small molecules and nucleic acids.

The term "GDF-9 activity" refers to one or more of physiologically growth-regulatory or morphogenetic activities associated with active GDF-9 protein. Assays for measuring GDF-9 activity in vivo and in vitro are known in the art. Examples of some of the more frequently used bioassays include the following:

(1) synthesis of progesterone, prostaglandin $E_2$, in granulosa cells (U.S. Pat. No. 6,680,174; Elvin et al., *Proc. Natl. Acad. Sci. USA* 97:10288-10293 (2000));

(2) induction of expression of a GDF-9 induced gene, including hyaluronan synthase, cyclooxygenase 2 (COX2), steroidogenic acute regulatory protein (StAR), luteinizing hormone (LH) receptors, activin/inhibin p, follistatin, and gremlin (U.S. Pat. No. 6,680,174; Elvin et al., Proc. Natl. Acad. Sci. USA 97:10288-10293 (2000));

(3) induction of proliferation of rat ovarian granulosa cells (Vitt et al., Biol. Reprod. 67:473-480 (2002); Liao et al., J. Biol. Chem. 279:17391-17396 (2004));

(4) mucification and expansion of mouse cumulus cells (Buccione et al., Dev. Biol. 138:16-25 (1990); Salustri et al., Dev. Biol. 138:26-32 (1990); Elvin et al., Mol. Endocrinol. 13:1035-1048 (1999));

(5) induction of the CAGA promoter fused to a luciferase reporter gene in P19 carcinoma cells (Mazerbourg et al., Mol. Endocrinol. 18:653-665 (2004));

(6) effect on the differentiation of mesenchymal stem cells to functionally competent osteoblasts (Jaiswal et al., J. Cell. Biochem. 64:295-312 (1997)); (7) receptor binding assay (Vitt et al., Biol. Reprod. 67:473-480 (2002));

(8) phosphorylation of Smads proteins (Mazerbourg et al., Mol. Endocrinol. 18:653-665 (2004)); and (9) receptor phosphorylation (Boyle et al., Methods Enzymol. 201B:110-149 (1991); Luo et al., Methods Enzymol. 201:149-152 (1991); Wrana et al., Mol. Cell. Biol. 14:944-950 (1994); Weiser, et al., EMBO J. 14:2199-2208 (1995)).

The term "BMP-15 inhibitor" and its cognates such as "antagonist," "neutralizing," and "downregulating" refer to a compound (or its property as appropriate), which acts as an inhibitor of biological activity of BMP-15. A BMP-15 inhibitor may, for example, bind to and neutralize the activity of BMP-15; decrease BMP-15 expression levels; affect stability or conversion of the precursor molecule to the active, mature form; interfere with the binding of BMP-15 to one or more receptors; or it may interfere with intracellular signaling of a BMP-15 receptor. The term "direct BMP-15 inhibitor" generally refers to any compound that directly downregulates the biological activity of BMP-15. A molecule "directly downregulates" the biological activity of BMP-15 if it downregulates the activity by interacting with a BMP-15 gene, a BMP-15 transcript, a BMP-15 ligand, or a BMP-15 receptor. The terms "neutralize," "neutralizing," "inhibitory," and their cognates refer to a reduction in the activity of BMP-15 by a BMP-15 inhibitor, relative to the activity of BMP-15 in the absence of the same inhibitor. The reduction in activity is preferably at least about 10%, 20%, 30%, 40%, 50%, 60%, 70%, 80%, 90%, or higher.

BMP-15 inhibitors that can block the activity of BMP-15 are useful in the invention. Such inhibitors may interact with BMP-15 itself. Alternatively, inhibitors may interact with a BMP-15 receptor (such as ALK6 or BMPRII) or other binding partner, for example. Inhibitors may reduce or block the binding of BMP-15 to its receptor and/or the activity of the receptor after binding of BMP-15. Inhibitors, of course, may interact with both BMP-15 and a second factor, such as its receptor. In this regard, BMP-15 inhibitors include antibodies (against BMP-15 and/or a BMP-15 receptor), modified soluble receptors, other proteins (including those that bind to BMP-15 and/or a BMP-15 receptor), modified forms of BMP-15 or fragments thereof, propeptides, peptides, and mimetics of all of these inhibitors. Nonproteinaceous inhibitors include, for example, small molecules and nucleic acids.

The term "BMP-15 activity" refers to one or more of physiologically growth-regulatory or morphogenetic activities associated with active BMP-15 protein. Assays for measuring BMP-15 activity in vivo and in vitro are known in the art. Examples of some of the more frequently used bioassays include the following (1) induction of proliferation of rat ovarian granulosa cells (Vitt et al., Biol. Reprod. 67:473-480 (2002); Liao et al., J. Biol. Chem. 279:17391-17396 (2004));

(2) induction of expression of granulosa cell kit ligand (Otsuka et al., Proc. Natl. Acad. Sci. USA 99:8060-8065 (2002));

(3) inhibition of follicle-stimulating hormone (FSH) receptor expression (Otsuka et al., J. Biol. Chem. 276: 11387-11392 (2001));

(4) suppression of FSH-induced progesterone synthesis (Otsuka et al., J. Biol. Chem. 275:39523-39528 (2000));

(5) suppression of FSH-induced expression of steroidogenic acute regulator protein (StAR), P450 side chain cleavage enzyme (P450 scc), 3β-hydroxysteroid dehydrogenase (3β-HSD), LH receptor, and inhibin/activin subunits (α, βA, and βB) in granulosa cells (Moore et al., Mol. Cell. Endocrinol. 234:67-73 (2005));

(6) effect on the differentiation of mesenchymal stem cells to functionally competent osteoblasts (Jaiswal et al., J. Cell. Biochem. 64:295-312 (1997);

(7) receptor binding assay (Vitt et al., Biol. Reprod. 67:473-480 (2002));

(8) phosphorylation of Smads proteins (Mazerbourg et al., Mol. Endocrinol. 18:653-665 (2004)); and (9) receptor phosphorylation (Boyle et al., Methods Enzymol. 201B:110-149 (1991); Luo et al., Methods Enzymol. 201:149-152 (1991); Wrana et al., Mol. Cell. Biol. 14:944-950 (1994); Weiser, et al., EMBO J. 14:2199-2208 (1995)).

The GDF-9 and BMP-II inhibitors are optionally glycosylated, pegylated, or linked to another nonproteinaceous polymer. Inhibitors of GDF-9 or BMP-15 may be modified to have an altered glycosylation pattern (i.e., altered from the original or native glycosylation pattern). As used herein, "altered" means having one or more carbohydrate moieties added or deleted, and/or having one or more glycosylation sites added or deleted as compared to the original inhibitor. Addition of glycosylation sites to the inhibitors may be accomplished by altering the amino acid sequence to contain glycosylation site consensus sequences well known in the art. Another means of increasing the number of carbohydrate moieties is by chemical or enzymatic coupling of glycosides to the amino acid residues of the inhibitor. These methods are described in WO 87/05330, and in Aplin et al., Crit. Rev. Biochem. 22:259-306 (1981). Removal of any carbohydrate moieties present on the receptor may be accomplished chemically or enzymatically as described by Sojar et al., Arch. Biochem. Biophys. 259:52-57 (1987); Edge et al., Anal. Biochem. 118:131-137 (1981); and by Thotakura et al., Meth. Enzymol. 138:350-359 (1987).

The GDF-9 and BMP-15 inhibitors useful in the methods of the invention may also be tagged with a detectable or functional label. Detectable labels include radiolabels such as $^{125}$I, $^{131}$I or $^{99}$Tc, which may be attached to the inhibitors using conventional chemistry known in the art. Labels also include enzyme labels such as horseradish peroxidase or alkaline phosphatase. Labels further include chemical moieties such as biotin, which may be detected via binding to a specific cognate detectable moiety, e.g., labeled avidin.

1. Antibodies

Antibodies that inhibit GDF-9 activity may be used in the methods of the invention. Also useful in the methods of the invention are antibodies that inhibit BMP-15 activity.

The term "antibody," as used herein, refers to an immunoglobulin or a part thereof, and encompasses any polypeptide comprising an antigen-binding site regardless of the source, species of origin, method of production, and characteristics. As a non-limiting example, the term "antibody" includes human, orangutan, mouse, rat, goat, sheep, and chicken antibodies. The term includes but is not limited to polyclonal, monoclonal, monospecific, polyspecific, non-specific, humanized, camelized, single-chain, chimeric, synthetic, recombinant, hybrid, mutated, and CDR-grafted antibodies. For the purposes of the present invention, it also includes, unless otherwise stated, antibody fragments such as Fab, F(ab')2, Fv, scFv, Fd, dAb, VHH (also referred to as nanobodies), and other antibody fragments that retain the antigen-binding function.

Antibodies can be made, for example, via traditional hybridoma techniques (Kohler and Milstein, Nature 256: 495-499 (1975)), recombinant DNA methods (U.S. Pat. No. 4,816,567), or phage display techniques using antibody libraries (Clackson et al., Nature 352: 624-628 (1991); Marks et al., J. Mol. Biol. 222: 581-597 (1991)). For various other antibody production techniques, see Antibodies: A Laboratory Manual, eds. Harlow et al., Cold Spring Harbor Laboratory, 1988.

The term "antigen-binding domain" refers to the part of an antibody molecule that comprises the area specifically binding to or complementary to a part or all of an antigen. Where an antigen is large, an antibody may only bind to a particular part of the antigen. The "epitope" or "antigenic determinant" is a portion of an antigen molecule that is responsible for specific interactions with the antigen-binding domain of an antibody. An antigen-binding domain may be provided by one or more antibody variable domains (e.g., a so-called Fd antibody fragment consisting of a VH domain). An antigen-binding domain can comprise an antibody light chain variable region (VL) and an antibody heavy chain variable region (VH). Antibodies from camels and llamas (Camelidae, camelids) include a unique kind of antibody, which is formed by heavy chains only and is devoid of light chains. The antigen-binding site of such antibodies is one single domain, referred to as VHH. These have been termed "camelized antibodies" or "nanobodies". See e.g. U.S. Pat. No. 5,800,988, U.S. Pat. No. 6,005,079, International Application No. WO 94/04678, and International Application No. WO 94/25591, which are incorporated herein by reference.

The term "repertoire" refers to a genetically diverse collection of nucleotides, e.g., DNA, sequences derived wholly or partially from sequences that encode expressed immunoglobulins. The sequences are generated by in vivo rearrangement of, e.g., V, D, and J segments for H chains and, e.g., V and J segment for L chains. Alternatively, the sequences may be generated from a cell line by in vitro stimulation and in response to which rearrangement occurs. Alternatively, part or all of the sequences may be obtained by combining, e.g., unrearranged V segments with D and J segments, by nucleotide synthesis, randomized mutagenesis, and other methods as disclosed in U.S. Pat. No. 5,565,332.

The term "specific interaction," or "specifically binds," or the like, means that two molecules form a complex that is relatively stable under physiologic conditions. The term is also applicable where, e.g., an antigen-binding domain is specific for a particular epitope, which is carried by a number of antigens, in which case the antibody carrying the antigen-binding domain will be able to bind to the various antigens carrying the epitope. Thus, an antibody may specifically bind, for example, GDF-9 and BMP-15, as long as it binds to an epitope that is carried by both.

Specific binding is characterized by a high affinity and a low to moderate capacity. Nonspecific binding usually has a low affinity with a moderate to high capacity. Typically, the binding is considered specific when the affinity constant Ka is higher than $10^6$ M$^{-1}$, or preferably higher than $10^8$ M$^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc.

The phrase "substantially as set out" means that the relevant CDR, VH, or VL domain will be either identical or highly similar to the specified regions of which the sequence is set out herein. For example, such substitutions include 1 or 2 out of any 5 amino acids in the sequence of a CDR(H1, H2, H3, L1, L2, or L3).

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure.

a. Antibodies Against GDF-9 or BMP-15

According to the methods described above, antibodies can be developed that specifically bind to the GDF-9 protein itself. These antibodies will be effective in the methods of the invention if they inhibit an activity of GDF-9, for example if they block binding of GDF-9 to its receptor. Antibodies that are most effective in this invention will have the property of binding specifically to GDF-9 of the GDF-9/GDF-9 receptor complex. Such antibodies may be capable of binding mature GDF-9 with high affinity, and may bind the mature protein in monomeric form, homodimer form, and/or heterodimer form, for example with BMP-15.

Antibodies against GDF-9 have been described in the art and are contemplated for use in the invention, for example, as set forth in U.S. Pat. No. 6,191,261.

Neutralizing antibodies for GDF-9 have been described in the art and are contemplated for use in the present invention. mAb-GDF9-53 is a specific anti-human GDF9 neutralizing monoclonal antibody (Gilchrist et al., Biol. Reprod. 71:732-739 (2004)). The immunizing peptide for this antibody was a synthetic 32 amino acid peptide corresponding to a peptide sequence close to the C-terminus of human GDF-9. Epitope mapping revealed that mAb-GDF9-53 recognizes a short 4-aa peptide sequence, EPDG, which is located approximately in the middle of the immunizing peptide. Alignment of C-terminal GDF-9 and BMP-15 amino acid sequences from several vertebrate species indicated that the EPDG sequence is highly conserved between species, but has a low level of similarity to the corresponding region in BMP-15. mAB-GDF9-53 exhibits strong immunoaffinity for recombinant mouse GDF-9, and very low cross-reactivity with BMP-15. Other anti-human GDF-9 antibodies with neutralizing activity described in Gilchrist et al. include mAb-GDF9-22, mAb-GDF9-19, mAb-GDF9-37.

According to the methods described above, antibodies can also be developed that specifically bind to the BMP-15 protein itself. These antibodies will be effective in the invention if they inhibit an activity of BMP-15, for example if they block binding of BMP-15 to its receptor. Antibodies that are most effective in this invention will have the property of binding specifically to BMP-15 of the BMP-15/BMP-15 receptor complex. Such antibodies may be capable of binding mature BMP-15 with high affinity, and may bind the mature protein in monomeric form, homodimer form, and/or heterodimer form, for example with GDF-9.

Antibodies against BMP-15 have been described in the art and are contemplated for use in the invention, for example, as set forth in U.S. Patent Pub. Nos. 2004/0267003 and 2004/0092007.

b. Antibodies Against GDF-9 Receptor or BMP-15 Receptor

According to the methods described above, antibodies can be developed that bind to the GDF-9 receptor. These antibodies will be effective in the invention if they block the binding of GDF-9 to its receptor or if they block the activity of the receptor after binding of GDF-9. Antibodies can be developed against the whole receptor protein, or against only the extracellular domain. Antibodies may be developed against ALK5 (Genbank Accession No. NP_004603), ALK5 variants, BMPRII (Genbank Accession No. NP_001195), BMPRII variants, and other receptors for GDF-9. For example, polyclonal and monoclonal (Clone 141229) antibodies to mouse ALK5 are available from R and D Systems (Minneapolis, Minn.); polyclonal and monoclonal (Clone 73805) antibodies to mouse human BMPRII are available from R and D Systems.

Similarly, antibodies can be developed that bind to the BMP-15 receptor. These antibodies will be effective in the invention if they block the binding of BMP-15 to its receptor or if they block the activity of the receptor after binding of BMP-15. Antibodies can be developed against the whole receptor protein, or against only the extracellular domain. Antibodies may be developed against ALK6 (Genbank Accession No. NP_001194), ALK6 variants, BMPRII (Genbank Accession No. NP_001195), BMPRII variants, and other receptors for BMP-15. For example, a mouse ALK6 polyclonal antibody is available from R and D Systems (Minneapolis, Minn.), as are human recombinant ALK-6/Fc chimera and mouse recombinant ALK-6/Fc chimera antibodies (R and D Systems, Minneapolis, Minn.), and human/mouse ALK-6 monoclonal antibodies (clone 88614; R and D Systems, Minneapolis, Minn.)).

2. Modified Soluble Receptors

Modified soluble receptors of GDF-9 may be used in the invention. Such modified sSoluble receptors may comprise all or part of the extracellular domain (also referred to as the ectodomain) of a GDF-9 receptor, such as ALK5 or BMPRII. The amino acid sequence of the ALK5 receptor, including description of the extracellular domain, specific fragments and variants of the receptor, are set forth in Genbank Accession No. NP_004603.

In one embodiment, soluble receptors may comprise all or part of the extracellular domain of BMPRII, which is a receptor for both GDF-9 as well as BMP-15. The amino acid sequence of BMPRII, including descriptions of the extracellular domain, specific fragments and variants of the receptor, are set forth in Genbank Accession No. NP_001195. A BMPRII ectodomain-Fc fusion protein which inhibits GDF-9 is set forth in Vitt et al., Biol. Reprod. 67:473-480 (2002).

In another embodiment, modified soluble receptors of BMP-15 may be used in the invention. Such modified sSoluble receptors may comprise all or part of the extracellular domain of a BMP-15 receptor, such as ALK6 or BMPRII. The amino acid sequences of the ALK6 receptor, including description of the extracellular domain, specific fragments and variants of the receptor, are set forth in Genbank Accession No. NP_001194, for example. An ALK6 ectodomain-Fc fusion protein is set forth in Vitt et al., Biol. Reprod. 67:473-480 (2002).

Soluble receptors may be produced recombinantly or by chemical or enzymatic cleavage of the intact receptor. The modified soluble receptors of the invention will bind GDF-9 and/or BMP-15 in the blood stream, reducing the ability of GDF-9 and/or BMP-15 to bind to its native receptor(s) in the body. In such a way, these modified soluble receptors inhibit activity of GDF-9 and/or BMP-15.

a. Receptor Fusions

The modified soluble receptors of the invention may be made more stable by fusion to another protein or portion of another protein. Increased stability is advantageous for therapeutics as they can be administered at a lower dose or at less frequent intervals. Fusion to at least a portion of an immunoglobulin, such as the constant region of an antibody, optionally an Fc fragment of an immunoglobulin, can increase the stability of a modified soluble receptor or other proteins of the invention. (See, e.g., Spiekermann et al., J. Exp. Med. 196: 303-310 (2002)).

3. Other Proteins

Other proteins that inhibit GDF-9 activity may be used in the methods of the invention. Such proteins can interact with GDF-9 itself, inhibiting its activity or binding to its receptor. Alternatively, inhibitors can interact with a GDF-9 receptor (such as ALK5 or BMPIIR) and may be effective in compositions or methods if they block the binding of GDF-9 to its receptor or if they block the activity of the receptor after binding of GDF-9. Inhibitors, of course, may interact with both GDF-9 and its receptor. Proteins that inhibit BMP-15 activity may also be used in the methods of the invention, by interacting with BMP-15 itself and/or its receptors.

a. Proteins Binding to GDF-9 or BMP-15

Proteins that bind to GDF-9 and inhibit its activity, including binding to its receptor, are acceptable for use in the methods of the invention. While some proteins are known, additional proteins can be isolated using screening techniques, an ALK5 or BMPIIR binding assay, or reporter gene assays described above. Samples of proteins may be screened, as well as libraries of proteins. Proteins that bind to BMP-15 and inhibit its activity may also be used in the methods of the invention.

i. GDF-9 and BMP-15 Propeptides

GDF-9 propeptide can be used as an inhibitor of GDF-9. To increase the in vivo half life of naturally occurring GDF-9 propeptides, a GDF-9 propeptide inhibitor may be modified and/or stabilized to improve pharmacokinetic properties, such as circulatory half-life (Massague, J., Ann. Rev. Cell Biol., 6:597-641 (1990); Jiang, et al., BBRC 315:525-531 (2004); Gregory et al., J. Biol. Chem. 280:27970-27980 (2005)).

In one embodiment, BMP-15 propeptide can be used as an inhibitor of BMP-15. To increase the in vivo half life of naturally occurring BMP-15 propeptides, the invention a BMP-15 propeptide inhibitor may be modified and/or stabilized to improve pharmacokinetic properties, such as circulatory half-life.

Such modified propeptides include fusion proteins comprising a propeptide and an Fc region of an IgG molecule (as a stabilizing protein). These inhibitors may comprise a GDF-9 or BMP-15 propeptide or a fragment or variant of said propeptide which retains one or more biological activities of the propeptide. The propeptides used in the invention may be synthetically produced, derived from naturally occurring (native) GDF-9 or BMP-15 propeptides, or be produced recombinantly, using any of a variety of reagents, host cells and methods which are well known in the art of genetic engineering. In one embodiment, the modified propeptide comprises a human propeptide covalently linked to an IgG molecule or a fragment thereof. The propeptide may be linked directly to the Fc region of the IgG molecule, or linked to the Fc region of the IgG molecule via a linker peptide (Jiang, et al., *BBRC* 315:525-531 (2004); Gregory et al., *J. Biol. Chem.* 280: 27970-27980 (2005)). Other stabilizing modification strategies are described in WO 02/068650, which is hereby incorporated by reference in its entirety.

ii Dominant Negative GDF-9 and BMP-15 Proteins

BMP-15 mutant proteins can be used as an inhibitor in the methods of the invention. The naturally occurring BMP-15 variant, Y235C-BMP-15, carries a non-conservative substitution in the pro region of BMP-15, and has a dominant negative effect on wild-type BMP-15 activity both in vivo and in vitro (Di Pasquale et al., *Am. J. Hum. Genet* 75:106-111 (2004)). The present invention also contemplates the use of GDF-9 mutant proteins, including dominant negative proteins, in the methods of the invention.

iii. Follistatin and Follistatin-Domain Containing Proteins

Follistatin binds to BMP-15 and can be used as an inhibitor of BMP-15 (Otsuka et al., *Biochem. Biophys. Res. Commun.* 289:961-966 (2001)). Accordingly, the invention provides proteins comprising at least one follistatin domain to modulate the level or activity of BMP-15, and may be used for treating disorders that are related to the modulation of the level or activity of BMP-15.

Both follistatin itself and follistatin domain containing proteins (described in U.S. Patent Pub. Nos. 2003/0162714 and 2003/0180306) may be used in the compositions and methods of the invention.

Proteins containing at least one follistatin domain will bind and inhibit GDF-9. Examples of proteins having at least one follistatin domain include, but are not limited to follistatin, follistatin-like related gene (FLRG), FRP (flik, tsc 36), agrins, osteonectin (SPARC, BM40), hevin (SC1, mast9, QR1), IGFBP7 (mac25), and U19878. GASP1 and GASP2 are other examples of proteins comprising at least one follistatin domain.

A follistatin domain, as stated above, is defined as an amino acid domain or a nucleotide domain encoding for an amino acid domain, characterized by cysteine rich repeats. A follistatin domain typically encompasses a 65-90 amino acid span and contains 10 conserved cysteine residues and a region similar to Kazal serine protease inhibitor domains. In general, the loop regions between the cysteine residues exhibit sequence variability in follistatin domains, but some conservation is evident. The loop between the fourth and fifth cysteines is usually small, containing only 1 or 2 amino acids. The amino acids in the loop between the seventh and eighth cysteines are generally the most highly conserved containing a consensus sequence of (G,A)-(S,N)-(S,N,T)-(D,N)-(G,N) followed by a (T,S)-Y motif. The region between the ninth and tenth cysteines generally contains a motif containing two hydrophobic residues (specifically V, I, or L) separated by another amino acid.

The term protein comprising at least one A follistatin domain-containing protein will comprise refers to proteins comprising at least one, but possibly more than one, follistatin domain. The term also refers to any variants of such proteins (including fragments; proteins with substitution, addition, or deletion mutations; and fusion proteins) that maintain the known biological activities associated with the native proteins, especially those pertaining to BMP-15 binding activity, including sequences that have been modified with conservative or non-conservative changes to the amino acid sequence.

These proteins may be derived from any source, natural or synthetic. The protein may be human or derived from animal sources, including bovine, chicken, murine, rat, porcine, ovine, turkey, baboon, and fish.

Proteins comprising at least one follistatin domain, which may bind BMP-15, may be isolated using a variety of methods. For example, one may use affinity purification using BMP-15. In addition, one may use a low stringency screening of a cDNA library, or use degenerate PCR techniques using a probe directed toward a follistatin domain. As more genomic data becomes available, similarity searching using a number of sequence profiling and analysis programs, such as Motif-Search (Genetics Computer Group, Madison, Wis.), ProfileSearch (GCG), and BLAST (NCBI) could be used to find novel proteins containing significant homology with known follistatin domains. In an embodiment of the invention, proteins comprising at least one follistatin domain specifically bind to mature BMP-15 or a fragment thereof, whether it is in monomeric form, active dimer form, or complexed in a BMP-15 latent complex, with an affinity of between 0.001 and 100 nM, or between 0.01 and 10 nM, or between 0.1 and 1 nM.

b. Proteins Binding to GDF-9 or BMP-15 Receptors

Proteins that bind to a GDF-9 receptor (such as ALK5 or BMPIIR) and inhibit the binding of GDF-9 to the receptor or the activity of the receptor itself are acceptable for use within the scope of the invention. Similarly, proteins that bind to a BMP-15 receptor (such as ALK6 or BMPRII) and inhibit the binding of BMP-15 to the receptor as the activity of the receptor itself are acceptable for use within the scope of the invention. Such proteins can be isolated using screening techniques and the assay or reporter gene assays described above. In one embodiment, the receptor binding proteins are antibodies. Samples of proteins may be screened, as well as libraries of proteins.

c. Fusions with any of the Binding Proteins

Fusion proteins of any of the proteins that bind to GDF-9, BMP-15, a GDF-9 receptor, or a BMP-15 receptor can be made more stable by fusion to another protein or portion of another protein. Increased stability is advantageous for therapeutics as they can be administered at a lower dose or at less frequent intervals. Fusion to at least a portion of an immunoglobulin, such as the constant region, optionally an Fc fragment of an immunoglobulin, can increase the stability of these proteins. The preparation of such fusion proteins is well known in the art and can be performed easily. (See, e.g., Spiekermann et al., *J. Exp. Med.,* 196:303-310 (2002)).

d. GDF-9 and BMP-15 Immunizing Peptides

The term "vaccine" as used herein refers to a composition or compound that induces a protective immune response, including either an antibody response or a cellular response. For example, a GDF-9 "vaccine" induces an immune response that antagonizes GDF-9 function. GDF-9 vaccines are set forth in U.S. Pat. No. 6,030,617. GDF-9 and BMP-15 immunogens for use as vaccines can be homologous GDF-9 or BMP-15 proteins which have been modified by introduction of one single or a few foreign, immunodominant and promiscuous T cell epitopes, while substantially preserving the tertiary structure of the protein; see e.g. WO 01/05820, which is hereby incorporated by reference. GDF-9 and BMP-15 peptides have been administered to sheep in short-term and long-term immunizations (Juengel et al., *Biol. Reprod.* 70:557-561 (2003); Juengel et al., *Biol. Reprod.* 67:1777-1789 (2002); McNatty et al., *Reprod.* 128:3790386 (2004)).

4. Mimetics of GDF-9 and BMP-15 Inhibitors

Mimetics of GDF-9 inhibitors may be used in the methods of the invention. Any synthetic analogue of these GDF-9 inhibitors, especially those with improved in vitro characteristics such as having a longer half-life, or being less easily degraded by the digestive system, are useful.

Mimetics of antibodies against GDF-9, antibodies against GDF-9 receptor, modified soluble receptors and receptor fusions, and other proteins binding to GDF-9 such as GDF-9 propeptide, mutated GDF-9 propeptide, follistatin and follistatin-domain containing proteins, and Fc fusions thereof may all be used in the invention.

These mimetics will be effective in the methods of the invention if they block the activity of GDF-9, namely if they block the binding of GDF-9 to its receptor. Mimetics that are most effective in this invention will have the property of binding specifically to GDF-9 or the GDF-9/GDF-9 receptor complex. Such mimetics may be capable of binding mature GDF-9 with high affinity, and may bind the mature protein whether it is in monomeric form, active dimer form, or complexed in a GDF-9 latent complex. Mimetics useful in the methods of the invention may inhibit GDF-9 activity in vitro and in vivo as demonstrated, for example, by inhibition of ALK5 or BMPIIR binding and reporter gene assays. Further, the disclosed mimetics may inhibit GDF-9 activity associated with negative regulation of skeletal muscle mass and bone density.

Mimetics of BMP-15 inhibitors may also be used in the methods of the invention. Any synthetic analogue of these BMP-15 inhibitors, especially those with improved in vitro characteristics such as having a longer half-life, or being less easily degraded by the digestive system, are useful.

Mimetics of antibodies against BMP-15, antibodies against BMP-15 receptor, modified soluble receptors and receptor fusions, and other proteins binding to BMP-15 such as BMP-15 propeptide, mutated BMP-15 propeptide, follistatin and follistatin-domain-containing proteins, and Fc fusions thereof may all be used in the invention.

These mimetics will be effective in the invention if they block the activity of BMP-15, namely if they block the binding of BMP-15 to its receptor. Mimetics that are most effective in this invention will have the property of binding specifically to BMP-15 or the BMP-15/BMP-15 receptor complex. Such mimetics may be capable of binding mature BMP-15 with high affinity, and may bind the mature protein whether it is in monomeric form, active dimer form, or complexed in a BMP-15 latent complex. Mimetics useful in the methods of the invention may inhibit BMP-15 activity in vitro and in vivo as demonstrated, for example, by inhibition of ALK6 or BMPIIR binding and reporter gene assays. Further, suitable mimetics may inhibit BMP-15 activity associated with negative regulation of skeletal muscle mass and bone density.

B. Nonproteinaceous Inhibitors

Nonproteinaceous inhibitors including, for example, small molecules and nucleic acids, may also be used in the methods of the invention 1. Small Molecules GDF-9 and BMP-15 inhibitors useful in the methods of the invention include small molecules. Small molecules include synthetic and purified naturally occurring GDF-9 and BMP-15 inhibitors. Small molecules can be mimetics or secretagogues.

Methods to identify small molecules that specifically target a protein of interest such as GDF-9 or BMP-15 are well known in the art. Small molecule and/or peptide libraries may be screened for inhibition of GDF-9 using any of the GDF-9 functional assays described above, including but not limited to expression of CAGA-luciferase, MSXII-luciferase, or BRE-luciferase in COS-7, CV-1, A204, or granulosa cells. Small molecule and/or peptide libraries may also be screened in a competitive radioligand binding assay of GDF-9 with its receptor, including, for example, a soluble receptor. The use of fluorescence resonance energy transfer (FRET)-based assays, such as the amplified luminescent proximity homogeneous assay (also known as "AlphaScreen," PerkinElmer, Boston, Mass.) may also be used to identify suitable small molecule inhibitors. In this embodiment, a GDF-9 peptide or BMP-15 peptide is coupled to a first "donor" population of beads, and used to identify interacting molecules within a population coupled to a second "acceptor" population of beads. Peptides interacting with GDF-9 or BMP-15 can be also used for screening assays. One GDF-9 peptide for use in such an assay is: SQLKWDNWIVAPHRYNPRYCKGDC (SEQ ID NO:5). Other examples of FRET-based assays include time-resolved FRET (e.g. the LANCE system of PerkinElmer, Boston, Mass.) to screen for inhibitors of ligand dimerization or to identify small molecules that interact with defined GDF-9 or BMP-15 peptides. In another embodiment, interactions with GDF-9 or BMP-15 of small molecules or peptides can be analyzed in real time using Biacore systems technology (Biacore International AB, Uppsala, Sweden). The invention also contemplates the use of additional screening assays, e.g. secondary and tertiary assays, to further identify the effect of such molecules on bone cell differentiation and function, and on bone density, for example, using assays described in detail above.

2. Nucleic Acids

The terms "polynucleotide," "oligonucleotide," and "nucleic acid" refer to deoxyribonucleic acid (DNA) and, where appropriate, to ribonucleic acid (RNA), or peptide nucleic acid (PNA). The term should also be understood to include nucleotide analogs, and single or double stranded polynucleotides (e.g., siRNA). Examples of polynucleotides include, but are not limited to, plasmid DNA or fragments thereof, viral DNA or RNA, RNAi, etc. The term "plasmid DNA" refers to double stranded DNA that is circular. The terms "siRNA" and "RNAi" refer to a nucleic acid which is a double stranded RNA that has the ability to induce degradation of mRNA thereby "silencing" gene expression.

Nucleic acids that that can block the activity of GDF-9 are useful in this invention. Such inhibitors may encode proteins that interact with GDF-9 itself. Alternatively, such inhibitors may encode proteins that can interact with a GDF-9 receptor (such as ALK5 or BMPIIR) and may be effective in the invention if the encoded proteins block the binding of GDF-9 to its receptor or if they block the activity of the receptor after binding of GDF-9. Inhibitors, of course, may encode proteins that interact with both GDF-9 and its receptor. Such nucleic acids can be used to express GDF-9 inhibitors of the invention.

Similarly, nucleic acids that that can block the activity of BMP-15 are useful in this invention. Such inhibitors may encode proteins that interact with BMP-15 itself. Alternatively, such inhibitors may encode proteins that can interact with a BMP-15 receptor (such as ALK5 or BMPIIR) and may be effective in the invention if the encoded proteins block the binding of BMP-15 to its receptor or if they block the activity of the receptor after binding of BMP-15. Inhibitors, of course, may encode proteins that interact with both BMP-15 and its receptor. Such nucleic acids can be used to express BMP-15 inhibitors of the invention.

The methods of the invention encompass the use of RNA interference ("RNAi") to reduce the expression of GDF-9 or a receptor of GDF-9 such as ALK5 or BMPIIR. RNAi can be initiated by introducing nucleic acid molecules, e.g. synthetic short interfering RNAs ("siRNAs") or RNA interfering agents, to inhibit or silence the expression of target genes.

See, for example, U.S. Patent Pub. Nos. 2003/0153519 and 2003/01674901, and U.S. Pat. Nos. 6,506,559, and 6,573,099.

An "RNA interfering agent" as used herein is any agent that interferes with or inhibits expression of a target gene or genomic sequence by RNA interference. Such RNA interfering agents include, but are not limited to, nucleic acid molecules including RNA molecules which are homologous to the target gene or genomic sequence, or a fragment thereof, short interfering RNA (siRNA), short hairpin or small hairpin (shRNA), and small molecules which interfere with or inhibit expression of a target gene by RNA interference.

As used herein, "inhibition of target gene expression" includes any decrease in expression or protein activity or level of the target gene or protein encoded by the target gene. The decrease may be of at least 30%, 40%, 50%, 60%, 70%, 80%, 90%, 95%, or 99% or more as compared to the expression of a target gene or the activity or level of the protein encoded by a target gene that has not been targeted by an RNA interfering agent.

An siRNA may be chemically synthesized, may be produced by in vitro transcription, or may be produced within a host cell. Typically, an siRNA is at least 15-50 nucleotides long, e.g., 20, 21, 22, 23, 24, 25, 26, 27, 28, 29, or 30 nucleotides in length. In one embodiment, the siRNA is a double stranded RNA (dsRNA) of about 15 to about 40 nucleotides in length, for example, about 15 to about 28 nucleotides in length, including about 19, 20, 21, or 22 nucleotides in length, and may contain a 3' and/or 5' overhand on each strand having a length of about 0, 1, 2, 3, 4, 5, or 6 nucleotides. In one embodiment, the siRNA can inhibit a target gene by transcriptional silencing. Preferably the siRNA is capable of promoting RNA interference through degradation or specific post-transcriptional gene silencing (PTGS) of the target messenger RNA.

siRNAs useful in the methods of the invention also include small hairpin RNAs (shRNAs). shRNAs are composed of a short (e.g. about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids and viral vectors.

The targeted region of the siRNA molecules of the present invention can be selected from a given target sequence. For example, nucleotide sequences can begin from about 25-100 nucleotides downstream of the start codon. Nucleotide sequences can contain 5' or 3' untranslated regions, as well as regions near the start codon. Methods for the design and preparation of siNRA molecules are well known in the art, including a variety of rules for selecting sequences as RNAi reagents (see, e.g., Boese et al., Methods Enzymol. 392:73-96 (2005)).

siRNA may be produced using standard techniques as described in Hannon, (2002) Nature, 418:244-251 (2002); McManus et al., (2002) Nat. Reviews, 3:737-747 (2002); Heasman, (2002) Dev. Biol., 243:209-214 (2002); Stein, (2001) J. Clin. Invest., 108:641-644 (2001); and Zamore, (2001) Nat. Struct. Biol., 8(9):746-750 (2001). Preferred siRNAs are 5-prime phosphorylated.

siRNA inhibitors can be used to target GDF-9, a GDF-9 receptor (including ALK5 and BMPRII), BMP-15, or a BMP-15 receptor (including ALK6 and BMPRII). The sequence of an siRNA for ALK5, which is associated with dose-dependent suppression of GDF-9 actions, is set forth in Mazerbourg et al., Mol. Endocrinol. 18:653-665 (2004)).

Antisense oligonucleotides can also be used to reduce the expression of GDF-9, a GDF-9 receptor, BMP-15, or a BMP-15 receptor. "Antisense," as used herein, refers to a nucleic acid capable of hybridizing to a portion of a coding and/or noncoding region of mRNA by virtue of sequence complementarity, thereby interfering with translation from the mRNA. Antisense nucleic acids may be produced using standard techniques as described in Antisense Drug Technology: Principles, Strategies, and Applications, 1st ed., eEd. Crooke, Marcel Dekker (, 2001). The sequence of a BMPRII antisense oligonucleotide is set forth in Vitt et al., Biol. Reprod. 67:473-480 (2002)).

Nucleic acids may be administered at a dosage from about 1 µg/kg to about 20 mg/kg, depending on the severity of the symptoms and the progression of the disease. The appropriate effective dose is selected by a treating clinician from the following ranges: about 1 µg/kg to about 20 mg/kg, about 1 µg/kg to about 10 mg/kg, about 1 µg/kg to about 1 mg/kg, about 10 µg/kg to about 1 mg/kg, about 10 µg/kg to about 100 µg/kg, about 100 µg to about 1 mg/kg, and about 500 µg/kg to about 1 mg/kg. Nucleic acid inhibitors may be administered via topical, oral, intravenous, intraperitoneal, intramuscular, intracavity, subcutaneous or transdermal means.

The nucleic acids may be obtained, isolated, and/or purified from their natural environment, in substantially pure or homogeneous form. Systems for cloning and expression of a polypeptide in a variety of different host cells are well known. Suitable host cells include bacteria, mammalian cells, and yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is E. coli. For other cells suitable for producing proteins from nucleic acids see Gene Expression Systems, eEds. Fernandez et al., Academic Press (1999).

Suitable vectors can be chosen or constructed, containing appropriate regulatory sequences, including promoter sequences, terminator sequences, polyadenylation sequences, enhancer sequences, selection or marker genes and other sequences as appropriate. Vectors may be plasmids or viral, e.g., phage, or phagemid, as appropriate. For further details see, e.g., Molecular Cloning: A Laboratory Manual, Sambrook et al., 2nd ed., Cold Spring Harbor Laboratory Press, (, 1989). Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, eEds. Ausubel et al., 2nd ed., John Wiley & Sons (, 1992).

A nucleic acid can be fused to other sequences encoding additional polypeptide sequences, for example, sequences that function as a marker or reporter. Examples of marker or reporter genes include-lactamase, chloramphenicol acetyltransferase (CAT), adenosine deaminase (ADA), aminoglycoside phosphotransferase (responsible for neomycin (G418) resistance), dihydrofolate reductase (DHFR), hygromycin-B-phosphotransferase (HPH), thymidine kinase (TK), lacZ (encoding-galactosidase), xanthine guanine phosphoribosyltransferase (XGPRT), luciferase, and many others known in the art.

II. Pharmaceutical Compositions and Methods of Administration

Methods of administering pharmaceutical compositions are known in the art. "Administration" is not limited to any particular delivery system and may include, without limitation, parenteral (including subcutaneous, intravenous, intramedullary, intraarticular, intramuscular, intracavity, or intraperitoneal injection) rectal, topical, transdermal, or oral (for example, in capsules, suspensions, or tablets). Administration to an individual may occur in a single dose or in continuous or intermittent repeat administrations, and in any of a variety of physiologically acceptable salt forms, and/or with an acceptable pharmaceutical carrier and/or additive as part of a pharmaceutical composition (described earlier).

Modulators of GDF-9 and BMP-15 may be formulated as pharmaceutical compositions. Physiologically acceptable salt forms and standard pharmaceutical formulation techniques and excipients are well known to persons skilled in the art (see, e.g., Physicians' Desk Reference (PDR) 2003, 57th ed., Medical Economics Company, 2002; and Remington: The Science and Practice of Pharmacy, eds. Gennado et al., 20th ed, Lippincott, Williams & Wilkins, 2000).

Modulators useful in the methods of the invention may be administered at a dosage from about 1 µg/kg to about 20 mg/kg, depending on the severity of the symptoms and the progression of the disease. The appropriate effective dose is selected by a treating clinician from the following ranges: about 1 µg/kg to about 20 mg/kg, about 1 µg/kg to about 10 mg/kg, about 1 µg/kg to about 1 mg/kg, about 10 µg/kg to about 1 mg/kg, about 10 µg/kg to about 100 µg/kg, about 100 µg to about 1 mg/kg, and about 500 µg/kg to about 1 mg/kg, for example.

In some embodiments, compositions used in the methods of the invention further comprise a pharmaceutically acceptable excipient. As used herein, the phrase "pharmaceutically acceptable excipient" refers to any and all solvents, dispersion media, coatings, antibacterial and antifungal agents, isotonic and absorption delaying agents, and the like, that are compatible with pharmaceutical administration. The use of such media and agents for pharmaceutically active substances are well known in the art. The compositions may also contain other active compounds providing supplemental, additional, or enhanced therapeutic functions. The pharmaceutical compositions may also be included in a container, pack, or dispenser together with instructions for administration.

A pharmaceutical composition is formulated to be compatible with its intended route of administration. Examples of such compositions include crystalline protein formulations, provided naked or in combination with biodegradable polymers (e.g., PEG, PLGA).

A modulator of the invention may be administered as a pharmaceutical composition in conjunction with carrier gels, matrices, excipients, or other compositions used for guided bone regeneration and/or bone substitution. Examples of such matrices include synthetic polyethylene glycol (PEG)-, hydroxyapatite, collagen and fibrin-based matrices, tisseel fibrin glue, etc. Excipients can include pharmaceutically acceptable salts, polysaccharides, peptides, proteins, amino acids, synthetic polymers, natural polymers, and surfactants.

In certain embodiments of the invention, the GDF-9 modulators and BMP-15 modulators are formulated for delivery as injectable or implantable compositions. The composition can be in the form of a cylindrical rod suitable for injecting or implanting in solid state into a body. In one embodiment, the injectable formulation includes the inhibitor and a hyaluronic acid ester, as described in detail in U.S. Patent Pub. No. 20050287135, which is hereby incorporated by reference. For example, Hyaff11p65 can be used as the hyaluronic acid. In another embodiment, the injectable formulation includes the modulator and a calcium phosphate material, such as amorphous apatitic calcium phosphate, poorly crystalline apatitic calcium phosphate, hydroxyapatite, tricalcium phosphate, fluorapatite and combinations thereof, as described in detail in U.S. Patent Pub. No. 20050089579, which is hereby incorporated by reference.

In certain embodiments, GDF-9 inhibitors and/or BMP-15 inhibitors may be administered in combination or concomitantly with other therapeutic compounds such as, e.g., bisphosphonate (nitrogen-containing and non-nitrogen-containing), apomine, testosterone, estrogen, sodium fluoride, strontium ranelate, vitamin D and its analogs, calcitonin, calcium supplements, selective estrogen receptor modulators (SERMs, e.g., raloxifene), osteogenic proteins (e.g., BMP-2), statins, RANKL inhibitors, Activators of Non-Genotropic Estrogen-Like Signaling (ANGELS), and parathyroid hormone (PTH). (Apomine is novel 1,1,-bisphosphonate ester, which activates farneion X activated receptor and accelerates degradation of HMG CoA (3-hydroxy-3-methylglytaryl-coenzyme A) reductase (see, e.g., U.S. Patent Pub. No. 2003/0036537 and references cited therein). In one preferred embodiment, inhibitors of GDF-9 or BMP-15 are co-administered with a bisphosphonate, including but not limited to alendronate, cimadronate, clodronate, EB-1053, etidronates, ibandronate, neridronate, olpadronate, pamidronate, risedronate, tiludronate, YH 529, zolendronate, and pharmaceutically acceptable salts, esters, acids, and mixtures thereof. In another preferred embodiment, inhibitors of GDF-9 and/or BMP-15 may be co-administered with one or more osteogenic proteins, including but not limited to BMP-2, BMP-4, BMP-5, BMP-6, BMP-7, BMP-9, BMP-10, BMP-12, BMP-13, and MP52. In one embodiment, an inhibitor of GDF-9 is co-administered with an inhibitor of BMP-3.

Administration of a therapeutic to an individual in accordance with the methods of the invention may also be by means of gene therapy, wherein a nucleic acid sequence encoding the modulator is administered to the patient in vivo or to cells in vitro, which are then introduced into a patient. For specific gene therapy protocols, see Morgan, Gene Therapy Protocols, 2nd ed., Humana Press (2000).

III. Methods of Screening and Diagnosis

The present invention can be used to identify subjects who are genetically predisposed to having altered bone density or presently have altered bone density. In one embodiment, to screen for and/or diagnose altered bone density, the relative level of GDF-9 or BMP-15 in a test sample from the subject and a control sample are compared. The presence of an altered level of GDF-9 or BMP-15 in the test sample is indicative of an altered bone density and/or a predisposition to developing an altered bone density in the subject. In another embodiment, the present invention provides a method for detecting the presence of a GDF-9 or BMP-15 variant nucleic acid sequence in a nucleic acid-containing sample, compared to a subject having a wild-type nucleic acid sequence.

In one embodiment, the level of GDF-9 and/or BMP-15 in a subject is elevated relative to a control sample, and the subject has decreased bone density or an increased risk of developing decreased bone density. In another embodiment, the level of GDF-9 or BMP-15 in a subject is decreased relative to a control sample, and the subject has increased bone density or an increased likelihood of developing increased bone density.

Anti-GDF-9 or BMP-15 specific antibodies or anti-GDF-9 or BMP-15 variant specific antibodies can be used to determine the level of the respective proteins in a sample. The invention provides a method for detecting GDF-9 or BMP-15 or variants thereof in a subject to be screened or diagnosed which includes contacting an anti-GDF-9 or BMP-15 antibody with a cell or protein and detecting binding to the antibody. The antibody can be directly labeled with a compound or detectable label which allows detection of binding to its antigen. Different labels and methods of labeling are known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. The level of GDF-9 or BMP-15 can be detected in samples isolated from biological fluids and tissues. Any specimen containing a detectable amount of antigen can be used. A preferred sample of this invention is bone tissue. The level of GDF-9 or BMP-15 in the suspect cell can be compared with the level in a normal cell to determine whether the subject is predisposed to altered bone density.

The antibodies of the invention are suited for use, for example, in immunoassays, including liquid phase or bound to a solid phase carrier. Immunoassays which use antibodies include competitive and non-competitive immunoassays in either a direct or indirect format, such as radioimmunoassays (RIA) and sandwich (immunometric) assays. Antibodies can also be used to detect GDF-9 or BMP-15 using immunohistochemical assays on physiological samples.

In another embodiment, the present invention provides a method for detecting the presence of a GDF-9 or BMP-15 variant nucleic acid sequence in a nucleic acid-containing test sample isolated from a subject, as compared to a control sample having a wild-type nucleic acid sequence.

"Variant," as used herein, refers to any GDF-9 or BMP-15 nucleic acid sequence which does not correspond to the wild-type GDF-9 or BMP-15 nucleic acid sequence, as well as the corresponding amino acid sequence. The methods of the invention include variants of segments of GDF-9 or BMP-15 which do not share sequence identity with the corresponding segment of the wild-type GDF-9 or BMP-15 sequence.

Variants useful in the methods and assays of the invention include alterations generated by a mutation, a restriction fragment length polymorphism, a single nucleotide polymorphism (SNP), a nucleic acid deletion, or a nucleic acid substitution naturally occurring or intentionally manipulated. A "deletion" is a change in the nucleotide sequence in which one or more nucleotide residues are absent. A "substitution" results from the replacement of one or more nucleotide residues with non-identical nucleotide residues.

Variants also include peptides, or full length proteins, that contain substitutions, deletions, or insertions into the protein backbone, that would still leave a 70% homology to the original protein over the corresponding portion. Examples of conservative substitutions involve amino acids that have the same or similar properties. Illustrative amino acid conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine.

The term "isolated" as used herein includes polynucleotides substantially free of other nucleic acids, proteins, lipids, carbohydrates or other materials with which it is naturally associated. Polynucleotide sequences of the invention include DNA and RNA sequences which encode GDF-9 or BMP-15 variants. It is understood that all polynucleotides encoding all or a portion of GDF-9 or BMP-15 variants are also included herein, such as naturally occurring, synthetic, and intentionally manipulated polynucleotides. The polynucleotides useful in the methods and assays of the invention include sequences that are degenerate as a result of the genetic code. A complementary sequence may include an antisense nucleotide. Also included are fragments (portions) of the above-described nucleic acid sequences that are at least 10-15 bases in length, which is sufficient to permit the fragment to specifically hybridize to DNA of the variant nucleic acid.

Nucleic acid sequences useful in the methods and assays of the invention can be obtained by any method known in the art. For example, DNA can be isolated by: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

The development of specific DNA sequences encoding GDF-9 or BMP-15, or variants thereof, can also be obtained by: 1) isolation of double-stranded DNA sequences from the genomic DNA; 2) chemical manufacture of a DNA sequence to provide the necessary codons for the polypeptide of interest; and 3) in vitro synthesis of a double stranded DNA sequence by reverse transcription of mRNA isolated from a eukaryotic donor cell. In the latter case, a double-stranded DNA complement of mRNA is formed, referred to as cDNA.

In a preferred embodiment, the present invention provides methods for identifying nucleic acid variants associated with altered bone density by detecting the presence of a target GDF-9 or BMP-15 variant nucleic acid sequence in sample isolated from a subject having altered bone density as compared to a subject having normal bone density and a wild type GDF-9 or BMP-15 nucleic acid sequence.

The present invention includes methods for identifying allelic variants in a subject. The subject may be homozygous or heterozygous for a GDF-9 or BMP-15 variant. As used herein, an "allele" is a gene or nucleotide sequence, such as a single nucleotide polymorphism (SNP), present in more than one form (different sequence) in a genome. "Homozygous", according to the present invention, indicates that the two copies of the gene or SNP are identical in sequence to the other allele. For example, a subject homozygous for the wild-type GDF-9 or BMP-15 gene contains at least two copies of the GDF-9 or BMP-15 wild-type sequence. Such a subject would not be predisposed to an altered bone density.

"Heterozygous," as used herein, indicates that two different copies of the allele are present in the genome, for example one copy of the wild-type allele and one copy of the variant allele. A subject having such a genome is heterozygous. "Heterozygous" also encompasses a subject having two different mutations in its GDF-9 or BMP-15 alleles.

One embodiment of the invention provides methods for developing an allelic profile of a subject for a GDF-9 or BMP-15 gene. "Allelic profile", as used herein, is a determination of the composition of a subject's genome in regard to the presence or absence, and the copy number, of the GDF-9 or BMP-15 allele or variants thereof.

In a preferred embodiment, the invention provides a method of determining predisposition of a subject to altered bone density. The method includes determining the GDF-9 or BMP-15 allelic profile of a subject by isolating the nucleic acid specimen from the subject which includes the GDF-9 or BMP-15 sequence and determining the presence or absence of a mutation in the GDF-9 or BMP-15 nucleic acid sequence. The invention also provides a diagnostic or prognostic method for determining the GDF-9 or BMP-15 allelic profile of a subject including isolating a nucleic acid sample from the subject; amplifying the nucleic acid with primers which hybridize to target sequences.

Any method which detects allelic variants can be used. For example, allele specific oligonucleotides (ASO's) can be used as probes to identify such variants. ASO probes can be any length suitable for detecting the sequence of interest. Preferably such probes are 10-50 nucleotides in length and will be detectably labeled by isotopic or nonisotopic methods. The target sequences can be optionally amplified and separated by gel electrophoresis prior to immobilization by Southern blotting. Alternatively, extracts containing unamplified nucleic acid can be transferred to nitrocellulose and probed directly as dot blots.

In addition, allele-specific alterations can be identified by coincidental restriction site alteration. Mutations sometimes alter restriction enzyme cleavage sites or, alternatively, introduce restriction sites were none had previously existed. The change or addition of a restriction enzyme recognition site can be used to identify a particular variant.

Primers used in the methods of the invention include oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15-22 or more nucleotides, although it may contain fewer nucleotides as long as the primer is of sufficient specificity to allow essentially only the amplification of the specifically desired target nucleotide sequence (i.e., the primer is substantially complementary).

Primers used according to the method of the invention are designed to be "substantially" complementary to each strand of mutant nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the mutant nucleotide sequence. Preferably, the 3' terminus of the primer that is extended has perfectly base paired complementarity with the complementary flanking strand.

Oligonucleotide primers can be used in any amplification process that produces increased quantities of target nucleic acid, including polymerase chain reaction. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized + and − strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The nucleic acid from any tissue specimen, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The mutant nucleotide sequence to be amplified may be a fraction of a larger molecule or can be present initially as a discrete molecule, such that the specific sequence constitutes the entire nucleic acid. It is not necessary that the sequence to be amplified be present initially in a pure form; it may be a minor fraction of a complex mixture, such as contained in whole human or animal DNA.

The amplified product may be detected by Southern blot analysis, without using radioactive probes. In such a process, for example, a small sample of DNA containing a very low level of mutant nucleotide sequence is amplified, and analyzed via a Southern blotting technique. The use of nonradioactive probes or labels is facilitated by the high level of the amplified signal.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

The probes of the present invention can be used for examining the distribution of the specific fragments detected, as well as the quantitative (relative) degree of binding of the probe for determining the occurrence of specific strongly binding (hybridizing) sequences.

The probes of the invention can be detectably labeled with an atom or inorganic radical, most commonly using radionuclides, but also heavy metals can be used. Any radioactive label may be employed which provides for an adequate signal and has sufficient half-life. Other labels include ligands, which can serve as a specific binding pair member for a labeled ligand, and the like. A wide variety of labels routinely employed in immunoassays can be used. Fluorescent compounds include fluorescein and its derivatives, rhodamine and its derivatives, dansyl, umbelliferone, and so forth. Chemiluminescers include luciferin, and 2,3-dihydrophtha-lazinediones (e.g., luminol).

Nucleic acids having a GDF-9 or BMP-15 variant detected by the methods of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008-1012, 1985), allele-specific oligonucleotide (ASO) probe analysis (Conner, et al., Proc. Natl. Acad. Sci. USA, 80:278, 1983), oligonucleotide ligation assays (OLAs) (Landegren, et al., Science, 241:1077, 1988), and the like.

The present in invention also provides kits for detecting altered levels or variances in GDF-9 and/or BMP-15. Such a kit may comprise a probe which is or can be detectably labeled. Such a probe may be an antibody or nucleotide specific for a target protein, or fragments thereof, or a target nucleic acid, or fragment thereof, respectively, wherein the target is indicative, or correlates with, the presence of GDF-9 or BMP-15, or variants thereof. For example, oligonucleotide probes of the present invention can be included in a kit and used for examining the presence of GDF-9 or BMP-15 variants, as well as the quantitative (relative) degree of binding of the probe for determining the occurrence of specific strongly binding (hybridizing) sequences, thus indicating the likelihood for an subject having or predisposed to having altered bone density.

In one embodiment, the kit utilizes nucleic acid hybridization to detect the target nucleic acid, the kit may also have containers containing nucleotide(s) for amplification of the target nucleic acid sequence. When it is desirable to amplify the target nucleic acid sequence, such as a variant nucleic acid sequence, this can be accomplished using oligonucleotide(s) that are primers for amplification.

In one embodiment, the kit may provides a container containing antibodies which bind to a target protein, or fragments thereof, or variants of such a protein, or fragments thereof. Thus, a kit may contain antibodies which bind to wild-type GDF-9 or BMP-15 or their variants. Such antibodies can be used to distinguish the presence of a particular GDF-9 or BMP-15 variant or the level of expression of such variants in a specimen.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

Example 1

Bone Mineral Density in GDF-9 Knockout Mice

The effect of a GDF-9 null mutation on bone mineral density was analyzed in female mice. GDF-9 knockout mice have previously been described (Dong et al., Nature 383:531-535 (1996)). Total, trabecular, and cortical volumetric bone mineral density (vBMD) were determined in 16-week old (Table 1) and 10-month old (Table 2) female mice as follows. Volumetric bone mineral density (vBMD, mg/cm$^3$) of the left femur was evaluated using an XCT Research peripheral Quantitative Computed Tomography densitometer (PQCT; Stratec Medizinetechnik, Pforzheim, Germany). One 0.5 mm thick pQCT slice obtained 2.5 mm proximal from the distal end of the femur was used to compute total and trabecular bone density for the distal femoral metaphysis. A second slice acquired 6 mm proximal from the end of the femur was used to assess cortical density. The tomographic slices had an in-plane pixel size of 0.07 mm. Following acquisition, the images were displayed and the region of interest including the entire femur for each scan was outlined. The soft tissue was automatically removed using an iterative algorithm and the density of the remaining bone (total density) in the first slice was determined. The outer 55% of the bone was then peeled away in a concentric spiral and the density of the remaining bone (trabecular density) of the first slice was reported in mg/cm$^3$. In the second slice, the boundary between cortical and trabecular bone was determined using an iterative algorithm and the density of the cortical bone was determined.

TABLE 1

Bone Density in 16-week old GDF-9 Knock out Female Mice

| Genotype | Total Density$^a$ | Trabecular Density$^a$ | Cortical Density$^a$ | Cortical Thickness$^b$ | Bone Length$^b$ |
|---|---|---|---|---|---|
| WT Female | 499.080 ± 7.781 | 136.370 ± 4.385 | 1190.030 ± 7.111 | 0.259 ± 0.004 | 14.92 ± 0.190 |
| KO Female | 544.920* ± 16.527 | 130.670 ± 6.557 | 1219.010* ± 10.145 | 0.278* ± 0.005 | 15.080 ± 0.166 |
| HET Female | 538.150** ± 8.217 | 148.750 ± 9.379 | 1195.080 ± 9.352 | 0.277** ± 0.003 | 15.410* ± 0.110 |

N = 10
$^a$Mean (mg/cm$^3$) ± SEM
$^b$Mean (mm) ± SEM
*p < 0.05 vs. corresponding wt value (Student T-Test)
**p < 0.01 vs. corresponding wt value (Student T-Test)

TABLE 2

Effect of GDF-9 Null Mutation Bone Mineral Density in 10 Month Old Female Mice

| Bone Mineral Density (g/cm$^3$) | Parameter | |
|---|---|---|
|  | WT (sFRP) (Mean ± SEM) | GDF-9 KO (Mean ± SEM) |
| Total | 481.6 ± 18.1 | 664.8 ± 44.7$^a$ |
| Trabecular | 109.0 ± 7.8 | 322.3 ± 62.9$^a$ |
| Cortical | 1229.2 ± 12.1 | 1337.6 ± 31.4$^a$ |

N = 8 animals/group
$^a$Significantly different from respective WT (sFRP) measurement (P < 0.05; Student's t-test); sFRP animals had been exposed transiently to high temperatures The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supersede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a bone disorder characterized by insufficient bone mass or bone density in a mammal, the method comprising administering to a mammal in need thereof a GDF-9 antibody or a GDF-9 specific RNA interfering agent (RNAi) in an amount and for a period of time sufficient to slow bone deterioration, restore lost bone, or stimulate new bone formation, thereby treating the bone disorder.

2. The method of claim 1, wherein the bone disorder is a bone degenerative disorder.

3. The method of claim 1, wherein the bone disorder is selected from the group consisting of osteopenia, osteomalacia, osteoporosis, osteomyeloma, osteodystrophy, Paget's disease, osteogenesis imperfecta, bone sclerosis, aplastic bone disorder, humoral hypercalcemic myeloma, multiple myeloma, and bone thinning following metastasis.

4. The method of claim 3, wherein the disorder is osteoporosis.

5. The method of claim 4, wherein the osteoporosis is post-menopausal, steroid-induced, senile, or thyroxin-use induced.

6. The method of claim 1, wherein the bone disorder in the mammal is associated with one or more of: hypercalcemia, chronic renal disease, kidney dialysis, primary and secondary hyperparathyroidism, inflammatory bowel disease, Krohn's disease, and long-term use of corticosteroids or GnRH agonists or antagonists.

7. A method of slowing bone deterioration, restoring lost bone, or stimulating new bone formation in a mammal, the method comprising
   (a) identifying a mammal in need of slower bone deterioration, restoration of lost bone, or stimulation of new bone formation, and
   (b) administering to the mammal in need thereof a therapeutically effective amount of a GDF-9 antibody or a GDF-9 specific RNA interfering agent (RNAi) in an amount and for a period of time sufficient to slow bone deterioration, restore lost bone, or stimulate new bone formation.

8. The method of claim 7, wherein the bone deterioration is characterized by a loss of bone mass.

9. The method of claim 8, further comprising measuring the loss of bone mass by measuring bone mineral density.

10. The method of claim 7, wherein the bone deterioration is characterized by degeneration of bone quality.

11. The method of claim 10, further comprising measuring the degeneration of bone quality by assessing microstructural integrity of the bone.

12. The method of claim 1 or 7, wherein the mammal is human.

13. The method of claim 1, wherein the antibody is a human antibody or a humanized derivative thereof.

14. The method of claim 1, wherein the antibody is selected from the group consisting of a polyclonal antibody, a monoclonal antibody, a monospecific antibody, a polyspecific antibody, a non-specific antibody, a humanized antibody, a camelized antibody, a single-chain antibody, a chimeric antibody, a synthetic antibody, a recombinant antibody, a hybrid antibody, a mutated antibody, and a CDR-grafted antibody.

15. The method of claim 1, wherein the antibody specifically binds to a mature GDF-9 protein.

16. The method of claim 1, wherein the antibody inhibits the signaling mediated by interaction between a GDF-9 polypeptide and its receptor.

17. The method of claim 1, wherein the RNA interfering agent is a double-stranded, short interfering RNA (siRNA).

18. The method of claim 17, wherein the siRNA inhibits GDF-9 by transcriptional silencing.

19. The method of claim 1 or 7, wherein the antibody or RNAi is administered systemically.

20. The method of claim 1 or 7, wherein the antibody or RNAi is administered at an effective dose chosen from the ranges of 1 µg/kg and 20 mg/kg, 1 µg/kg and 10 mg/kg, 1 µg/kg and 1 mg/kg, 10 µg/kg and 1 mg/kg, 10 µg/kg and 100 µg/kg, 100 µg/kg and 1 mg/kg, and 500 µg/kg and 1 mg/kg.

21. The method of claim 1 or 7, wherein the antibody or RNAi is administered repeatedly over a period of time of at least two weeks.

22. A method of increasing cortical bone density, the method comprising administering a therapeutically effective amount of a GDF-9 antibody or a GDF-9 specific RNA interfering agent (RNAi) to a mammal in need thereof, thereby increasing cortical bone density.

23. A method of increasing trabecular bone density, the method comprising administering a therapeutically effective amount of a GDF-9 antibody or a GDF-9 specific RNA interfering agent (RNAi) to a mammal in need thereof, thereby increasing trabecular bone density.

24. The method of claim 1 or 7, further comprising administering to the mammal one or more bone disorder treatment agents selected from the group consisting of bisphosphonates, calcitonin, estrogens, selective estrogen receptor modulators, parathyroid hormone, vitamins, and combinations thereof.

25. The method of claim 24, wherein the bone disorder treatment agent is a selective estrogen receptor modulator.

26. The method of claim 24, wherein the bone disorder treatment agent is a bisphosphonate.

27. The method of claim 1 or 7, further comprising administering to the mammal one or more osteogenic proteins.

28. The method of claim 27, wherein the osteogenic protein is selected from the group consisting of BMP-2, BMP-4, BMP-5, BMP-6, BMP-7, BMP-9, BMP-10, BMP-12, BMP-13, and MP52.

29. The method of claim 27, wherein the osteogenic protein is an inhibitor of BMP-3.

30. The method of claim 14, wherein the antibody is monoclonal.

31. The method of claim 1, wherein the antibody is an antibody fragment selected from the group consisting of a Fab, F(ab')2, Fv, scFv, Fd, dAb, VHH, and nanobody fragment.

32. The method of claim 1, wherein the antibody reduces the activity of GDF-9 by at least 10%.

33. The method of claim 1 wherein the antibody binds to GDF-9 with a Ka of at least $10^6$ $M^{-1}$.

34. The method of claim 1 wherein the antibody is a GDF-9 neutralizing antibody.

35. The method of claim 34, wherein the GDF-9 neutralizing antibody comprises up to 2 amino acid substitutions out of any 5 amino acids in the sequence of a CDR, VH, or VL of an antibody selected from the group consisting of mAb-GDF-9-53, mAb-GDF-9-22, mAb-GDF-9-19, and mAb-GDF-9-37.

36. The method of claim 35, wherein the GDF-9 neutralizing antibody is selected from the group consisting of mAb-GDF-9-53, mAb-GDF-9-22, mAb-GDF-9-19, and mAb-GDF-9-37.

37. The method of claim 1 wherein the antibody binds an epitope comprising amino acids 433-436 of SEQ ID NO:2.

38. A method of treating a bone disorder characterized by insufficient bone mass or bone density in a mammal, the method comprising administering to a mammal in need thereof a GDF-9 neutralizing antibody in an amount and for a period of time sufficient to slow bone deterioration, restore lost bone, or stimulate new bone formation, thereby treating the bone disorder.

* * * * *

SEQUENCE LISTING

```
<160> NUMBER OF SEQ ID NOS: 5

<210> SEQ ID NO 1
<211> LENGTH: 2020
<212> TYPE: DNA
<213> ORGANISM: human

<400> SEQUENCE: 1
gaaaagagag gaaagctaaa taaccaagta aatctgtatc taattaacaa attggctaaa      60
taaggtgtta tcagctgctt gatatagagc tgataaaatc ttcagctagg catacttgag     120
gcctgattac agaagtgacc gtagtccacc cacacacctg aaatttattt aagagaccaa     180
gctaggctct tcctggcctt taggaagagg actggcatgg agaaatatgt tcctcactag     240
ttctcccaag ccatggcacg tcccaacaaa ttcctccttt ggttttgctg ctttgcctgg     300
ctgtgttttc ctattagcct tggttctcag gcttctgggg gagaagctca gattgctgct     360
agtgctgagt tggaatctgg ggctatgcct tggtccttgc tgcagcatat agatgagaga     420
gacagagctg gcctccttcc cgcgcttttc aaagttctat ctgttgggcg aggtgggtca     480
cctaggctgc agccagactc cagagctttg cactacatga agaagctcta taagacatat     540
gctaccaagg aagggattcc taaatccaat agaagtcacc tctacaacac tgttcggctc     600
ttcaccccct gtacccggca caagcaggct cctggagacc aggtaacagg aatccttcca     660
tcagtggaac tgctatttaa cctggatcgc attactaccg ttgaacactt actcaagtca     720
gtcttgctgt acaatatcaa caactcagtt tcttttttcct ctgctgtcaa atgtgtgtgc     780
aatctaatga taaaggagcc aaagtcttct agcaggactc tcggcagagc tccatactca     840
tttaccttta actcacagtt tgaatttgga aagaaacaca aatggattca gattgatgtg     900
accagcctcc ttcaaccttt agtggcctcc aacaagagaa gtattcacat gtctataaat     960
tttacttgca tgaaagacca gctggagcat ccttcagcac agaatggttt gtttaacatg    1020
actctggtgt ccccctcact gatcttatat ttgaatgaca caagtgctca ggcttatcac    1080
agctggtatt cccttcacta taaaggagg ccttcccagg gtcctgacca ggagagaagt     1140
ctgtctgcct atcctgtggg agaagaggct gctgaggatg ggagatcttc ccatcaccgt    1200
caccgcagag gtcaggaaac tgtcagttct gaattgaaga agccctttggg cccagcttcc    1260 ttcaatctga gtgaatactt cagacaattt cttcttcccc aaaatgagtg tgagctccat    1320
gactttagac ttagctttag tcagctgaag tgggacaact ggattgtggc tccgcacagg    1380
tacaaccctc gatactgtaa aggggactgt ccaagggcag ttggacatcg gtatggctct    1440
ccagttcaca ccatggtaca gaacatcatc tatgagaagc tggactcctc agtgccaaga    1500
ccgtcatgtg tacctgccaa atacagcccc ttgagtgttt tgaccattga gcccgatggc    1560
tcaattgcct ataaagagta cgaagatatg atagctacaa agtgcacctg tcgttaacaa    1620
atggtcctct taaaaccttg agcctatttg gcaaagtaac tactgtgtgc ctatgtgtgc    1680
cttcaagaga aagcttcata tattaagtct ctaaatgtag catatgttat ataaagagga    1740
gcctgtgtag gttagtacct tctatggcat ctatcaggat aaagggataa catcaattgt    1800
tgctacagag ccttttttta tttccaaatt taaatgaaat ataattattg tggagaactt    1860
```

-continued

```
tacattttt   tccttgagtg  atttttttc   ttttcatagg  agtcttattc  ttgatagga        1920 aaaaccctta  attagcatca  atcctggatg  gacttgcagc  tataaatagg  caattcagat       1980
tgctgtagtc  ttaatagaag  aataaatttc  tgtcaatggc                               2020
```

<210> SEQ ID NO 2
<211> LENGTH: 454
<212> TYPE: PRT
<213> ORGANISM: human

<400> SEQUENCE: 2

```
Met Ala Arg Pro Asn Lys Phe Leu Leu Trp Phe Cys Cys Phe Ala Trp
1               5                   10                  15

Leu Cys Phe Pro Ile Ser Leu Gly Ser Gln Ala Ser Gly Gly Glu Ala
            20                  25                  30

Gln Ile Ala Ala Ser Ala Glu Leu Glu Ser Gly Ala Met Pro Trp Ser
        35                  40                  45

Leu Leu Gln His Ile Asp Glu Arg Asp Arg Ala Gly Leu Leu Pro Ala
    50                  55                  60

Leu Phe Lys Val Leu Ser Val Gly Arg Gly Gly Ser Pro Arg Leu Gln
65                  70                  75                  80

Pro Asp Ser Arg Ala Leu His Tyr Met Lys Lys Leu Tyr Lys Thr Tyr
                85                  90                  95

Ala Thr Lys Glu Gly Ile Pro Lys Ser Asn Arg Ser His Leu Tyr Asn
            100                 105                 110

Thr Val Arg Leu Phe Thr Pro Cys Thr Arg His Lys Gln Ala Pro Gly
        115                 120                 125

Asp Gln Val Thr Gly Ile Leu Pro Ser Val Glu Leu Leu Phe Asn Leu
    130                 135                 140

Asp Arg Ile Thr Thr Val Glu His Leu Leu Lys Ser Val Leu Leu Tyr
145                 150                 155                 160

Asn Ile Asn Asn Ser Val Ser Phe Ser Ser Ala Val Lys Cys Val Cys
                165                 170                 175

Asn Leu Met Ile Lys Glu Pro Lys Ser Ser Ser Arg Thr Leu Gly Arg
            180                 185                 190

Ala Pro Tyr Ser Phe Thr Phe Asn Ser Gln Phe Glu Phe Gly Lys Lys
        195                 200                 205

His Lys Trp Ile Gln Ile Asp Val Thr Ser Leu Leu Gln Pro Leu Val
    210                 215                 220

Ala Ser Asn Lys Arg Ser Ile His Met Ser Ile Asn Phe Thr Cys Met
225                 230                 235                 240

Lys Asp Gln Leu Glu His Pro Ser Ala Gln Asn Gly Leu Phe Asn Met
                245                 250                 255

Thr Leu Val Ser Pro Ser Leu Ile Leu Tyr Leu Asn Asp Thr Ser Ala
            260                 265                 270

Gln Ala Tyr His Ser Trp Tyr Ser Leu His Tyr Lys Arg Arg Pro Ser
        275                 280                 285

Gln Gly Pro Asp Gln Glu Arg Ser Leu Ser Ala Tyr Pro Val Gly Glu
    290                 295                 300

Glu Ala Ala Glu Asp Gly Arg Ser Ser His His Arg His Arg Arg Gly
305                 310                 315                 320

Gln Glu Thr Val Ser Ser Glu Leu Lys Lys Pro Leu Gly Pro Ala Ser
                325                 330                 335

Phe Asn Leu Ser Glu Tyr Phe Arg Gln Phe Leu Leu Pro Gln Asn Glu
```

```
                340             345             350
Cys Glu Leu His Asp Phe Arg Leu Ser Phe Ser Gln Leu Lys Trp Asp
            355                 360                 365

Asn Trp Ile Val Ala Pro His Arg Tyr Asn Pro Arg Tyr Cys Lys Gly
        370                 375                 380

Asp Cys Pro Arg Ala Val Gly His Arg Tyr Gly Ser Pro Val His Thr
385                 390                 395                 400

Met Val Gln Asn Ile Ile Tyr Glu Lys Leu Asp Ser Ser Val Pro Arg
                405                 410                 415

Pro Ser Cys Val Pro Ala Lys Tyr Ser Pro Leu Ser Val Leu Thr Ile
            420                 425                 430

Glu Pro Asp Gly Ser Ile Ala Tyr Lys Glu Tyr Glu Asp Met Ile Ala
        435                 440                 445

Thr Lys Cys Thr Cys Arg
    450

<210> SEQ ID NO 3
<211> LENGTH: 1179
<212> TYPE: DNA
<213> ORGANISM: human

<400> SEQUENCE: 3
atggtcctcc tcagtattct tagaattctt tttctttgtg aactcgtgct tttcatggaa      60
cacagggccc aaatggcaga aggagggcag tcctctattg cccttctggc tgaggcccct     120
actttgcccc tgattgagga gctgctagaa aatcccctg cgaacagcc aaggaagccc       180 cggctcctag ggcattcact gcggtacatg ctggagttgt accggcgttc agctgactcg     240
catgggcacc tagagagaa ccgcaccatt ggggccacca tggtgaggct ggtgaagccc      300
ttgaccagtg tggcaaggcc tcacagaggt acctggcata tacagatcct gggctttcct    360
ctcagaccaa accaggact ataccaacta gttagagcca ctgtggttta ccgccatcat     420
ctccaactaa ctcgcttcaa tctctcctgc catgtggagc cctgggtgca gaaaaaccca    480
accaaccact tcccttcctc agaaggagat tcctcaaaac cttccctgat gtctaacgct    540
tggaaagaga tggatatcac acaacttgtt cagcaaaggt tctggaataa caagggacac    600
aggatcctac gactccgttt tatgtgtcag cagcaaaaag atagtggtgg tcttgagctc    660
tggcatggca cttcatcctt ggacattgcc ttcttgttac tctatttcaa tgatactcat    720
aaaagcattc ggaaggctaa atttcttccc aggggcatgg aggagttcat ggaaagggaa    780
tctcttctcc ggagaacccg acaagcagat ggtatctcag ctgaggttac tgcctcttcc    840
tcaaaacata gcgggcctga aaataaccag tgttccctcc acccttccca aatcagcttc    900
cgccagctgg gttgggatca ctggatcatt gctccccctt tctacacccc aaactactgt    960
aaaggaactt gtctccgagt actacgcgat ggtctcaatt cccccaatca cgccattatt   1020
cagaacctta tcaatcagtt ggtggaccag agtgtccccc ggccctcctg tgtcccgtat   1080
aagtatgttc caattagtgt ccttatgatt gaggcaaatg ggagtatttt gtacaaggag   1140
tatgagggta tgattgctga gtcttgtaca tgcagatga                           1179

<210> SEQ ID NO 4
<211> LENGTH: 392
<212> TYPE: PRT
<213> ORGANISM: human

<400> SEQUENCE: 4
```

```
Met Val Leu Leu Ser Ile Leu Arg Ile Leu Phe Leu Cys Glu Leu Val
1               5                   10                  15

Leu Phe Met Glu His Arg Ala Gln Met Ala Glu Gly Gly Gln Ser Ser
            20                  25                  30

Ile Ala Leu Leu Ala Glu Ala Pro Thr Leu Pro Leu Ile Glu Glu Leu
        35                  40                  45

Leu Glu Glu Ser Pro Gly Glu Gln Pro Arg Lys Pro Arg Leu Leu Gly
    50                  55                  60

His Ser Leu Arg Tyr Met Leu Glu Leu Tyr Arg Arg Ser Ala Asp Ser
65                  70                  75                  80

His Gly His Pro Arg Glu Asn Arg Thr Ile Gly Ala Thr Met Val Arg
                85                  90                  95

Leu Val Lys Pro Leu Thr Ser Val Ala Arg Pro His Arg Gly Thr Trp
                100                 105                 110

His Ile Gln Ile Leu Gly Phe Pro Leu Arg Pro Asn Arg Gly Leu Tyr
            115                 120                 125

Gln Leu Val Arg Ala Thr Val Val Tyr Arg His His Leu Gln Leu Thr
    130                 135                 140

Arg Phe Asn Leu Ser Cys His Val Glu Pro Trp Val Gln Lys Asn Pro
145                 150                 155                 160

Thr Asn His Phe Pro Ser Ser Glu Gly Asp Ser Ser Lys Pro Ser Leu
                165                 170                 175

Met Ser Asn Ala Trp Lys Glu Met Asp Ile Thr Gln Leu Val Gln Gln
            180                 185                 190

Arg Phe Trp Asn Asn Lys Gly His Arg Ile Leu Arg Leu Arg Phe Met
    195                 200                 205

Cys Gln Gln Gln Lys Asp Ser Gly Gly Leu Glu Leu Trp His Gly Thr
210                 215                 220

Ser Ser Leu Asp Ile Ala Phe Leu Leu Leu Tyr Phe Asn Asp Thr His
225                 230                 235                 240

Lys Ser Ile Arg Lys Ala Lys Phe Leu Pro Arg Gly Met Glu Glu Phe
                245                 250                 255

Met Glu Arg Glu Ser Leu Leu Arg Arg Thr Arg Gln Ala Asp Gly Ile
            260                 265                 270

Ser Ala Glu Val Thr Ala Ser Ser Lys His Ser Gly Pro Glu Asn
    275                 280                 285

Asn Gln Cys Ser Leu His Pro Phe Gln Ile Ser Phe Arg Gln Leu Gly
290                 295                 300

Trp Asp His Trp Ile Ile Ala Pro Pro Phe Tyr Thr Pro Asn Tyr Cys
305                 310                 315                 320

Lys Gly Thr Cys Leu Arg Val Leu Arg Asp Gly Leu Asn Ser Pro Asn
                325                 330                 335

His Ala Ile Ile Gln Asn Leu Ile Asn Gln Leu Val Asp Gln Ser Val
            340                 345                 350

Pro Arg Pro Ser Cys Val Pro Tyr Lys Tyr Val Pro Ile Ser Val Leu
    355                 360                 365

Met Ile Glu Ala Asn Gly Ser Ile Leu Tyr Lys Glu Tyr Glu Gly Met
    370                 375                 380

Ile Ala Glu Ser Cys Thr Cys Arg
385                 390

<210> SEQ ID NO 5
<211> LENGTH: 24
<212> TYPE: PRT
```

```
-continued

<213> ORGANISM: human

<400> SEQUENCE: 5

Ser Gln Leu Lys Trp Asp Asn Trp Ile Val Ala Pro His Arg Tyr Asn
1               5                   10                  15

Pro Arg Tyr Cys Lys Gly Asp Cys
            20
```